United States Patent [19]
Yoo et al.

[11] Patent Number: 5,849,753
[45] Date of Patent: Dec. 15, 1998

[54] PYRIDYL IMIDAZOLE DERIVATIVES AND PROCESSES FOR THE PREPARATION THEREOF

[75] Inventors: Sung-Eun Yoo; Kyu-Yang Yi; Sang-Hee Lee; Hye-Ryung Kim; Jee-Hee Suh; Nak-Jeong Kim; Seon-Ju Kim; Ok-Ja Cha, all of Daejeon; Young-Ah Shin, Chungjoo; Wha-Sup Shin, Daejeon; Sung-Hou Lee, Daejeon; Yi-Sook Jung, Daejeon; Byung-Ho Lee, Daejeon; Ho-Won Seo, Daejeon, all of Rep. of Korea

[73] Assignee: Korea Research Institute of Chemical Technology, Daejeon, Rep. of Korea

[21] Appl. No.: 682,684

[22] PCT Filed: Feb. 8, 1995

[86] PCT No.: PCT/KR95/00009

§ 371 Date: Jul. 25, 1996

§ 102(e) Date: Jul. 25, 1996

[87] PCT Pub. No.: WO95/21838

PCT Pub. Date: Aug. 17, 1995

[30] Foreign Application Priority Data

Feb. 8, 1994 [KR] Rep. of Korea .......................... 94-2354
Jun. 18, 1994 [KR] Rep. of Korea ....................... 94-13795
Jul. 25, 1994 [KR] Rep. of Korea ....................... 94-17900
Jan. 25, 1995 [KR] Rep. of Korea ......................... 95-1286

[51] Int. Cl.$^6$ ........................ A61K 31/435; C07D 471/04
[52] U.S. Cl. ............................................. 514/303; 546/118
[58] Field of Search ............................... 546/118; 514/303

[56] References Cited

FOREIGN PATENT DOCUMENTS 400974 12/1990 European Pat. Off. .

*Primary Examiner*—Bernard Dentz
*Attorney, Agent, or Firm*—Anderson Kill & Olick P.C.

[57] ABSTRACT

Substituted pyridyl imidazole derivatives of formula (I) inhibit effectively the action of angiotensin II and have a superior anti-hypertensive activity.

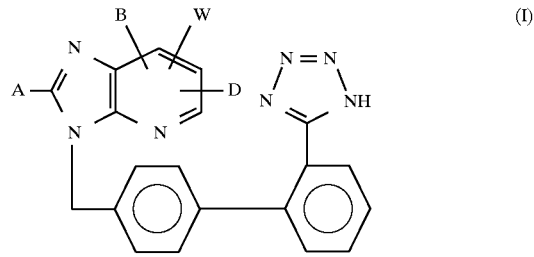

10 Claims, 2 Drawing Sheets

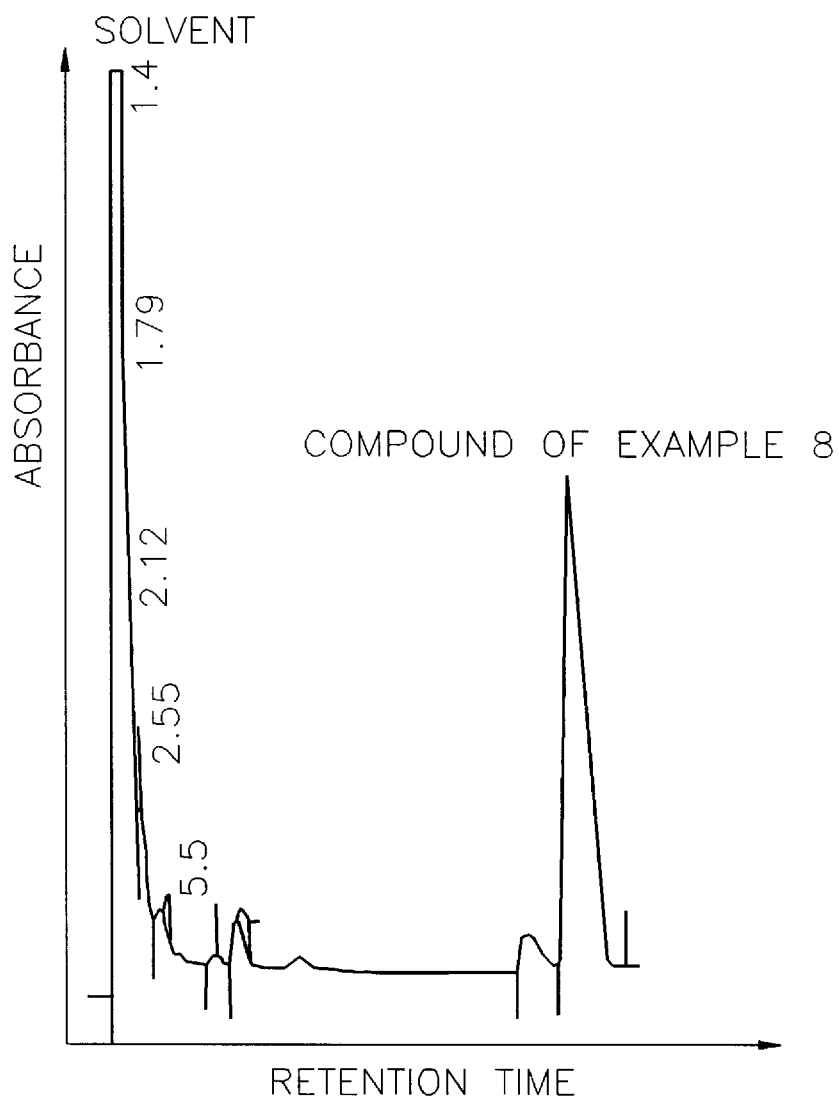

PYRIDYL IMIDAZOLE DERIVATIVES AND PROCESSES FOR THE PREPARATION THEREOF

This applicaton is a 371 of PCT/KR95/00009 filed Feb. 8, 1995.

FIELD OF THE INVENTION

The present invention relates to novel substituted pyridyl imidazole derivatives, processes for preparing them and pharmaceutical compositions containing same as active ingredients.

DESCRIPTION OF THE PRIOR ART

Various pyridyl imidazole derivatives, which can inhibit the action of angiotensin II, have been used for the treatment of hypertension caused by angiotensin II. Angiotensin II is produced, by an angiotensin converting enzyme, from angiotensin I, which is formed from angiotensinogen in blood plasma α-globin by the action of renin. Angiotensin II, which is a potent vaso-constrictor interacting with specific receptors on cell membrane, has been reported to cause hypertension in mammals including human beings.

Many studies have been made to search for an antagonist which inhibits the action of angiotensin II on the receptors of its target cell in order to suppress the elevation of blood pressure. As a result, many imidazole derivatives have been developed(see A. T. Chiu et al., *Eur. J. Pharm.*, 157, 13(1981); P. C. Wong et al., *J. Pharmacol. Exp. Ther.*, 247, 1(1988); P. C. Wong et al., *Hypertension*, 13, 489(1989), etc.).

For example, D. J. Carini et al. reported in *J. Med. Chem.*, 34, 2525(1990) imidazole derivatives of the following formula(A):

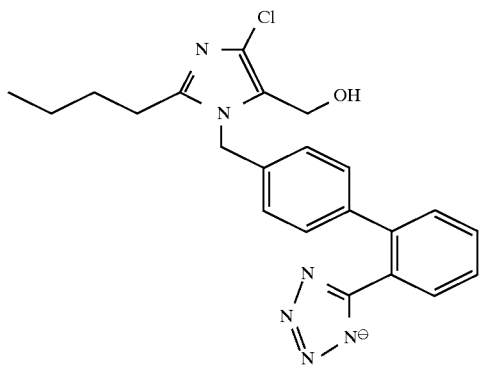

Further, EP No. 400,974 discloses imidazole derivatives of the following formula(B):

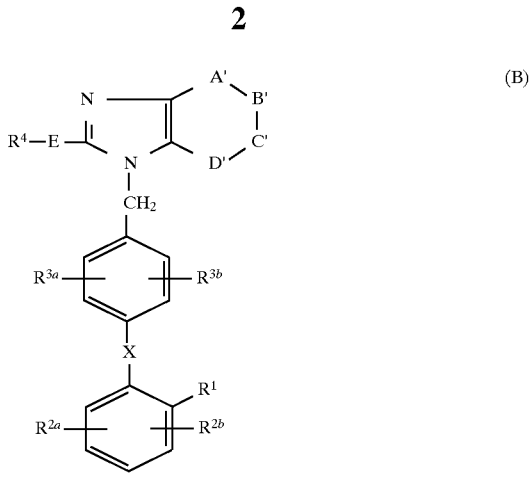

wherein: —A'—B'—C'—D'— represents a 6-membered heterocycle having 1 to 3 nitrogen atoms such as —C(R$^7$) =C(R$^7$)—C(R$^7$)=N— wherein each of R$_7$'s is independently a hydrogen atom, or a substituted alkyl or aryl group or heterocycle(e.g., —C(CH$_3$)=CH—C(CH$_3$)=N—).

However, needs have continued to exist for the development of imidazole derivatives which inhibit more effectively the activity of angiotensin II.

SUMMARY OF THE INVENTION

Accordingly, an object of the present invention is to provide novel substituted pyridyl imidazole derivatives of formula(I), and pharmacologically acceptable salts thereof, having an enhanced ability to suppress the activity of angiotensin II:

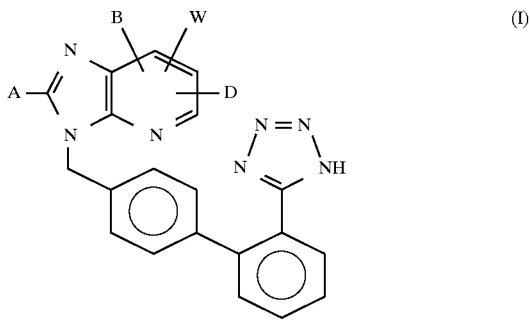

wherein: A is a straight, branched or cyclic C$_1$–C$_6$ alkyl group, OR$_1$, or NR$_2$R$_3$ wherein R$_1$, R$_2$ and R$_3$ are independently a hydrogen, or a straight, branched or cyclic C$_1$–C$_6$ alkyl group; B is a hydrogen, or a straight, branched or cyclic C$_1$–C$_6$ alkyl group; D is a hydrogen, a halogen, or a straight, branched or cyclic C$_1$–C$_6$ alkyl group, or

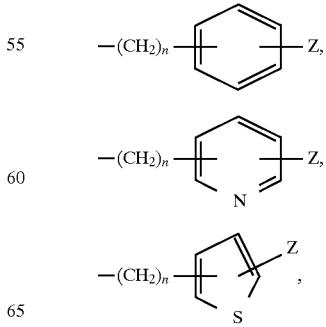

-continued

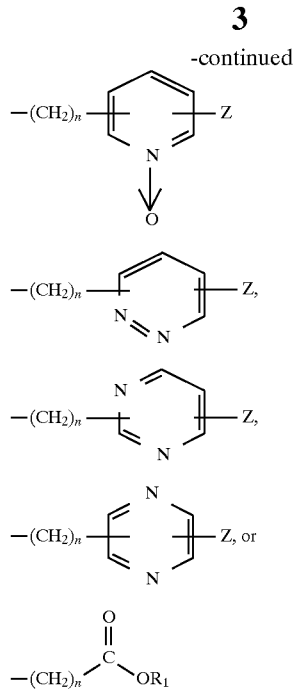

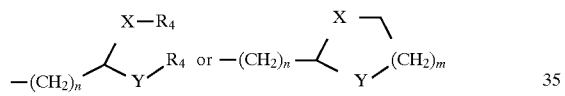

wherein Z is a hydrogen, $R_1$, $NO_2$, $(CH_2)_pOR_5$, $(CH_2)_pNR_2R_3$ or a halogen, n is 0 or an integer of 1 to 3, $R_1$, $R_2$ and $R_3$ are the same as defined above, p is 0 or an integer of 1 to 3, and $R_5$ is a hydrogen, a $C_1$–$C_6$ alkyl group or a phenyl group substituted with a $C_1$–$C_4$ alkyl; and W is

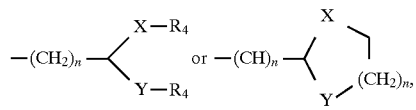

wherein X and Y are independently O or S, m is an integer of 1 to 4, n is the same as defined above and $R_4$ is a straight, branched or cyclic $C_1$–$C_4$ alkyl group.

It is another object of the present invention to provide processes for preparing the derivatives, and provide pharmaceutical compositions containing same as active ingredients.

DETAILED DESCRIPTION OF THE INVENTION

Figure 1A:
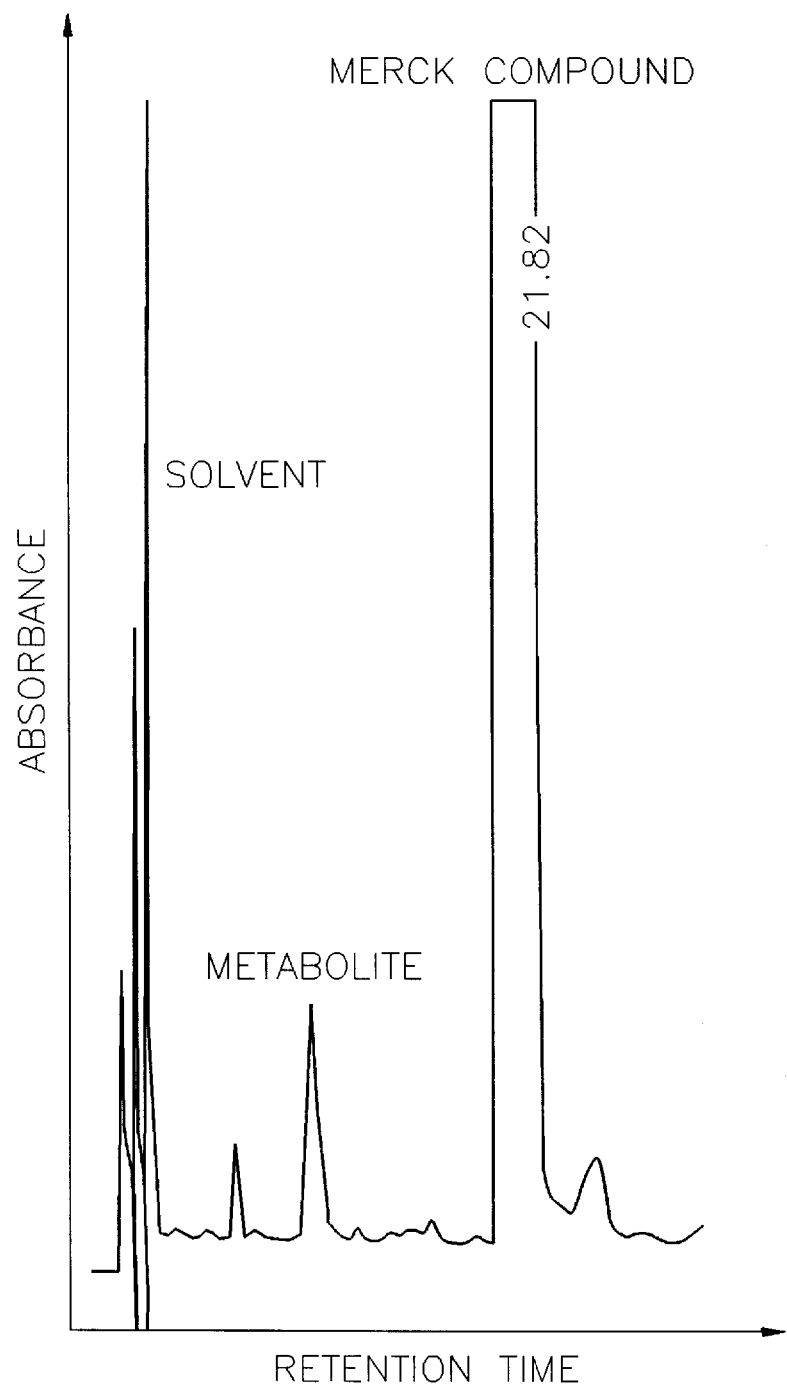
FIG. 1 is a HPLC chart showing the result of the enzyme digestion test of the Merck compound(FIG. 1A) and the present compound prepared in Example 8(FIG. 1B), respectively.

The present compound of formula(I) is characterized in that the substituent W has the structure of:

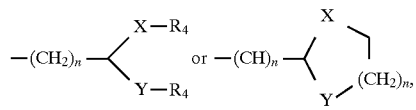

wherein $R_4$, X, Y, n and m have the same meanings as defined previously.

Among the compounds of formula(I), preferred are those wherein A is a straight, branched or cyclic $C_2$–$C_4$ alkyl group or $OR_1$ wherein $R_1$ is a straight, branched or cyclic $C_1$–$C_4$ alkyl group; B is a hydrogen or a straight, branched or cyclic $C_1$–$C_4$ alkyl group; D is H, F, Br, Cl, a straight, branched or cyclic $C_1$–$C_6$ alkyl group, or

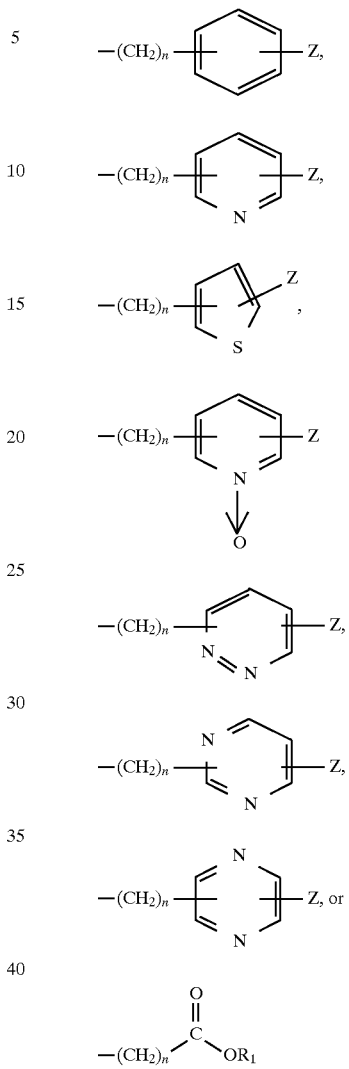

wherein Z is a hydrogen, $R_1$, $NO_2$, $(CH_2)_pOR_5$F, Br or Cl, n is 0, 1 or 2, $R_1$ is the same as defined above, p is 0, 1 or 2, and $R_5$ is a hydrogen, a $C_1$–$C_4$ alkyl group or a phenyl group substituted with a $C_1$–$C_4$ alkyl; and w is

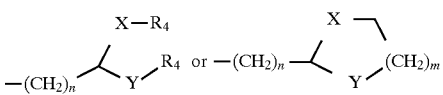

wherein X and Y are independently O or S, m is an integer of 1 to 3, n is the same as defined above and $R_4$ is a straight, branched or cyclic $C_1$–$C_4$ alkyl group.

The pyridyl imidazole derivatives of formula(I) of the present invention may be prepared by several methods depending on the substituents. For example, a compound of formula(I-1) may be prepared as described below:

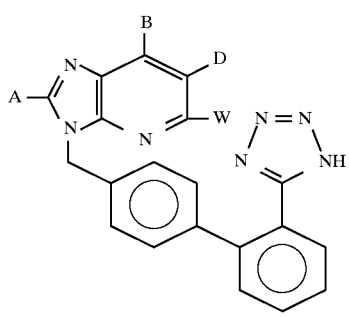
(I-1)

wherein A, B and W are the same as defined previously and the substituent D is

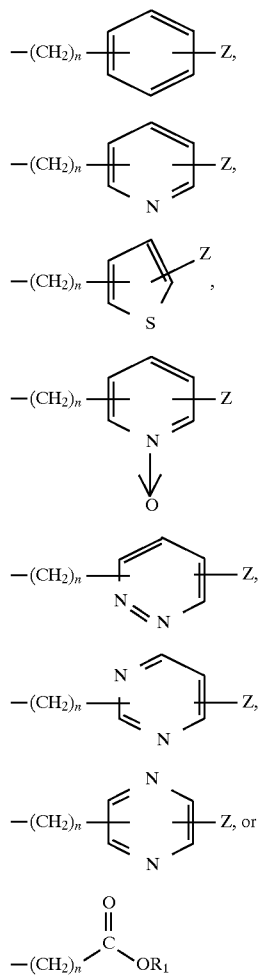

wherein Z is a hydrogen, $R_1$, $NO_2$, $(CH_2)_pOR_5$, $(CH_2)_pNR_2R_3$ or a halogen, n, p, $R_1$, $R_2$ and $R_3$ are the same as defined previously, and $R_5$ is a hydrogen or a phenyl group substituted with a $C_1$-$C_4$ alkyl.

A. Preparation of the compound of foumula(I-1) wherein n is 0

Amino pyridine compound of formula(II) is converted to a nitro compound of formula(III) by using an acid such as nitric acid-sulfuric acid, nitric acid-anhydrous acetic acid or sodium nitrate-sulfuric acid, which is then reduced to a compound of formula(IV) with a conventional reducing agent such as Fe—HCl or Pd—H. Thereafter, the compound (IV) is condensed with a carboxylic acid of A—COOH or an ester of A—COOR$_1$, wherein A and $R_1$ are the same as defined previously, to give a pyridyl imidazole derivative of formula(V):

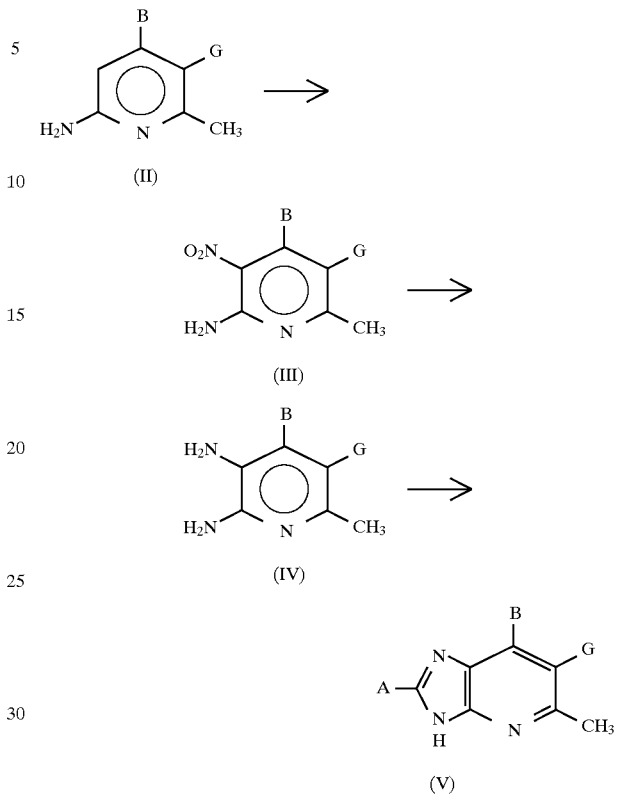

wherein A and B are the same as defined previously, and G is a halogen.

The pyridyl imidazole derivative of formula(V) is oxidized to N-oxide compound of formula(VI) using an oxidizing agent. Representative examples of the oxidizing agent are hydrogen peroxide, m-chloroperbenzoic acid, oxone and mixtures thereof. The N-oxide of formula(VI) is refluxed in the presence of anhydrous acetic acid to give an acetate of the compound of formula(VII); and, thereafter, the acetate is hydrolyzed with a base such as sodium hydroxide, potassium hydroxide, lithium hydroxide and mixtures thereof to give an imidazole compound of formula(VII):

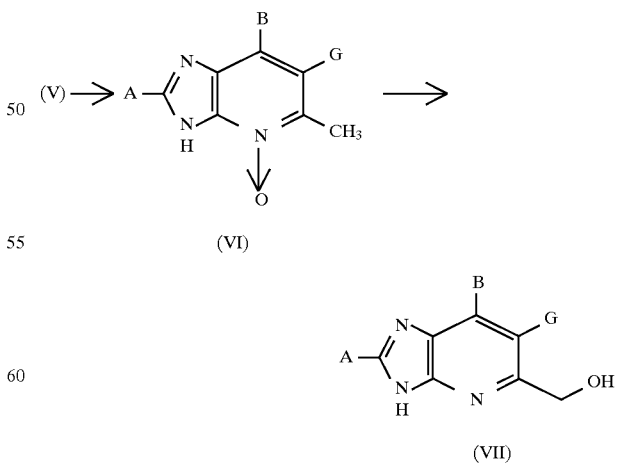

wherein A, B and G are the same as defined previously.

Then, the nitrogen atom in the imidazole ring of the compound(VII) is protected by a protecting group to give a compound of formula(VIII). The nitrogen protecting group may be a conventional one such as 3,4-dimethoxybenzyl or 2-oxo-2-phenylethyl group. The compound(VIII) is then reacted with a compound of formula(IX) in the presence of a palladium compound such as tetrakistriphenylphosphine palladium or palladium acetate to give a compound of formula(X):

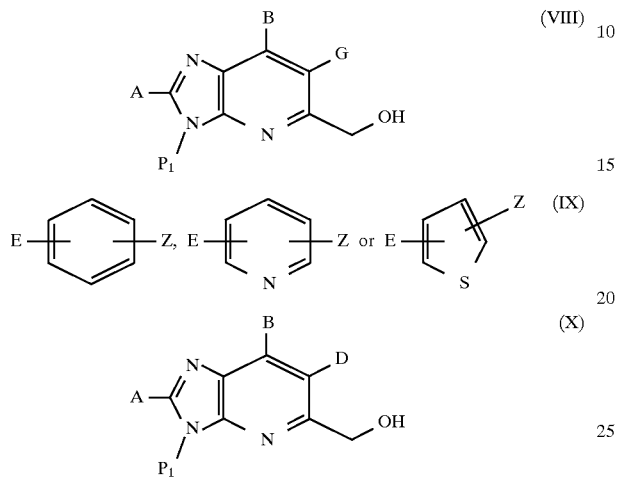

wherein: E is $-(CH=CH)_q-B(OH)_2$ or $-(CH=CH)_q-SnR_3$, q is 0 or 1, $P_1$ is a protecting group, and A, B, D, G, Z and $R_3$ are the same as defined previously.

In the above reaction, if q is 1, an olefin derivative is obtained, and the olefin group of the compound(X) is reduced to a compound of formula(I) by a conventional hydrogenation method.

Then, the compound(X) is deprotected to give a compound of formula(XI):

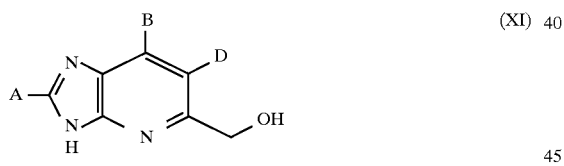

wherein A, B and D are the same as defined previously.

For example, when the protecting group $P_1$ in formula(X) s 2-oxo-2-phenylethyl group, it may be deprotected by using zinc powder; and in case that $P_1$ is 3,4-dimethoxybenzyl group, conc. sulfuric acid or trifluoroacetic acid may be used as the deprotecting agent.

The compound(XI) is then reacted with the compound of formula(XII) in the presence of a base such as sodium hydride, potassium carbonate and the like to give a compound of formula(XIII):

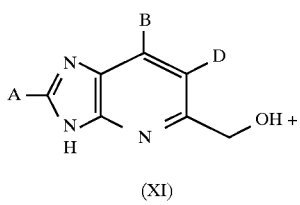

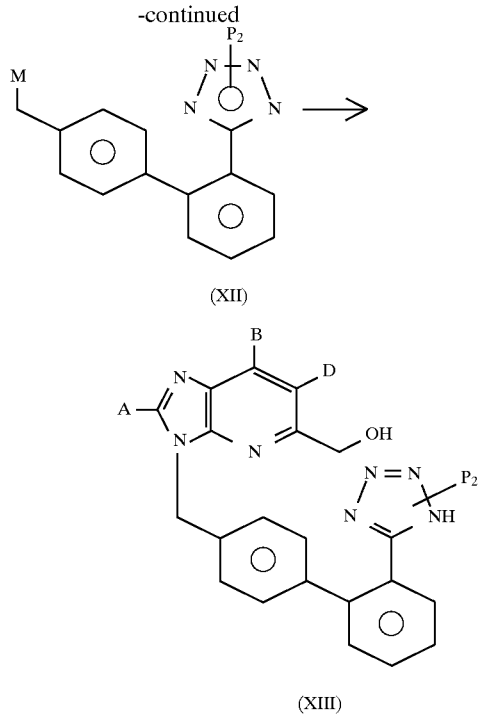

wherein: A, B and D are the same as defined previously, $P_2$ is a protecting group such as triphenylmethyl or 1-ethoxyethyl group, and M is a leaving group such as a halogen, tosylate or mesylate.

The compound(XIII) is oxidized with a conventional oxidizing agent such as dimethyl sulfoxide-oxalyl chloride, chromium trioxide or manganese dioxide to give a compound of formula(XIV), which is then reacted with $R_4XH$ or $HXCH_2(CH_2)_mYH$ in the presence of an acid catalyst to obtain the compound(I-1) of the present invention:

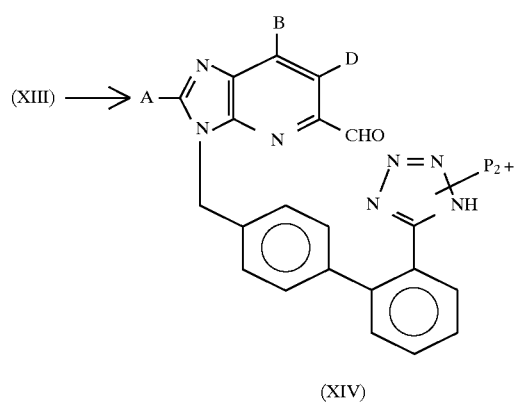

wherein A, B, D, $P_2$, $R_4$, X, Y and m are the same as defined previously.

Representative examples of the acid catalyst are hydrochloric acid, sulfuric acid and p-toluenesulfonic acid. The reactant $R_4XH$ or $HXCH_2(CH_2)_mYH$ may be used as a solvent; and, if desired, such other solvent as benzene and toluene may be used. The reaction may be conducted at a temperature ranging from 20° C. to a boiling point of the solvent; and, at this time, the protecting group $P_2$ is removed concurrently.

Another method for preparing the compound(XI) above is that the compound(V) is processed as in the conversion step of the compound(VIII) into the compound(X) to give a compound of formula(XV), which is then processed as in the conversion step of the compound(V) into the compound (VII):

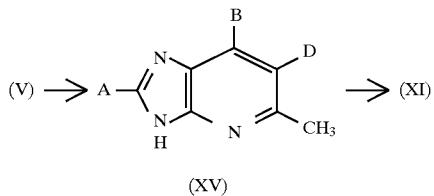

wherein A, B and D are the same as defined previously.

An alternative method for preparing the compound(XIV) is that the compound(XV) is oxidized with an oxidizing agent such as selenium dioxide or chromium trioxide to give a compound of formula(XVI), which is then processed as in the reaction step from the compound(XI) to compound (XIII):

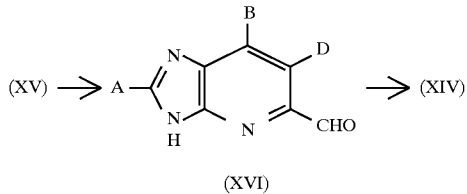

wherein A, B and D are the same as defined previously.

Another method for the preparation of the compound (XIII) is that the compound(XV) is processed as in the reaction step from the compound(XI) to the compound(XII) to obtain a compound of formula(XVIII), which is then processed as in the reaction step from the compound(V) to the compound(VII):

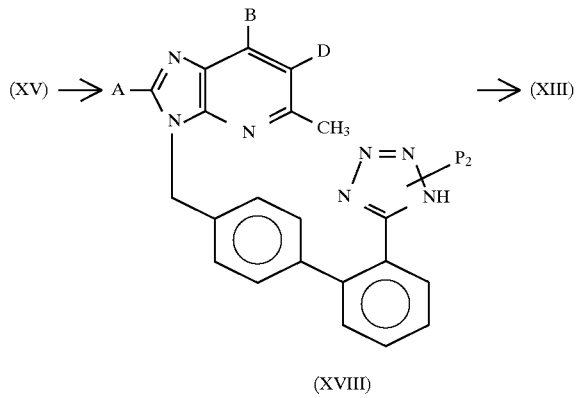

wherein A, B, D and $P_2$ are the same as defined previously.

Further, a different method for the preparation of the compound(XV) is that the compound(III) is processed as in the reaction step from the compound(VIII) to the compound (X) to give a compound of formula(XVII), which is then processed as in the reaction step from the compound(III) to the compound(V):

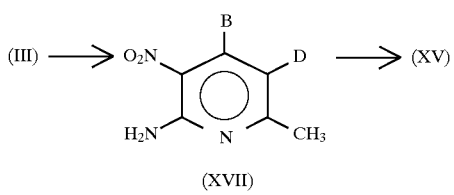

wherein B and D are the same as defined previously.

B. Preparation of the compound of foumula(I-1) wherein n is 1

At first, the OH group of the compound(XIII) is substituted with a leaving group, M, such as halogen, tosylate or mesylate by a conventional method and then the compound (XIII) is reacted with sodium cyanide or potassium cyanide to give a compound of formula(XIX), which is reduced with diisobutylaluminum hydride to give a compound of formula (XX). Thereafter, the compound(XX) is processed to give the compound(I-1) as in the reaction step from the compound(XIV) to the compound(I-1):

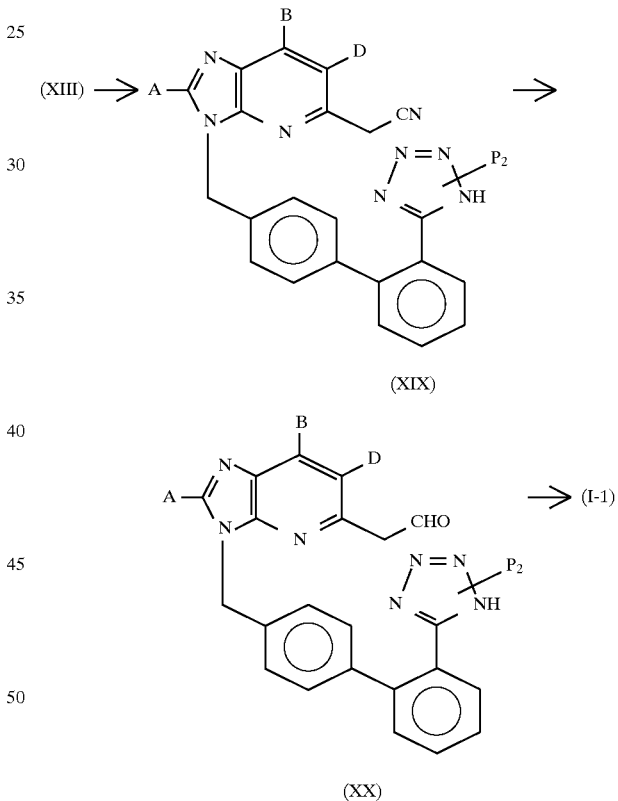

wherein A, B, D and P are the same as defined previously.

C. Preparation of the compound of foumula(I-1) wherein n is 2

The compound(XIV) is reacted with ethoxycarbonylmethyl triphenylphosphorane to give a compound of formula (XXI), which is hydrogenated to give a compound of formula(XXII) by conventional hydrogenation. The compound(XXII) is then reduced with diisobutyl aluminum hydride to the compound of formula(XXIII), which is processed as in the reaction step from the compound(XIV) to the compound(I-1) to give a compound of formula(I-1):

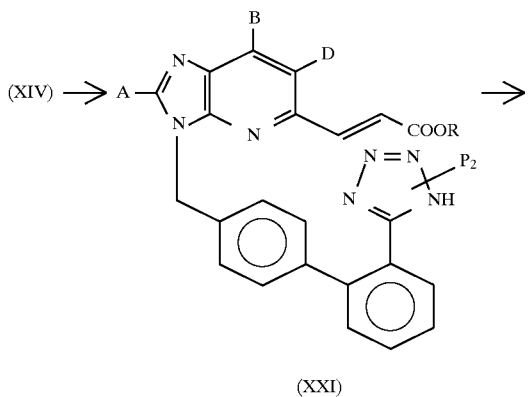

(XXI)

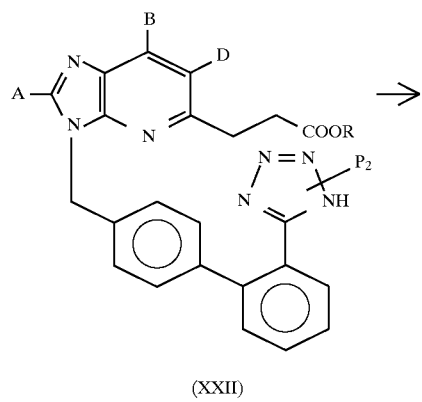

(XXII)

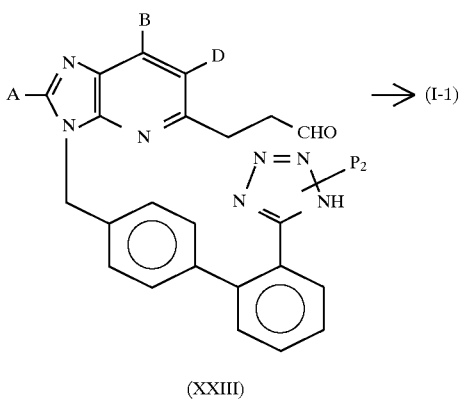

(XXIII)

wherein: A, B, D and $P_2$ are the same as defined previously, and R is a $C_1$–$C_4$ alkyl group.

D. Preparation of the compound of foumula(I-1) wherein n is 3

The compound(XXII) is reduced with a reducing agent such as sodium borohydride or lithium aluminum hydride to the compound of formula(XXIV), which is processed as in the reaction step from the compound(XIII) to the compound (XX) to give a compound of formula(XXV). Then, the compound(XXV) is processed as in the reaction step from the compound (XIV) to the compound(I-1) to give the compound of formula(I-1):

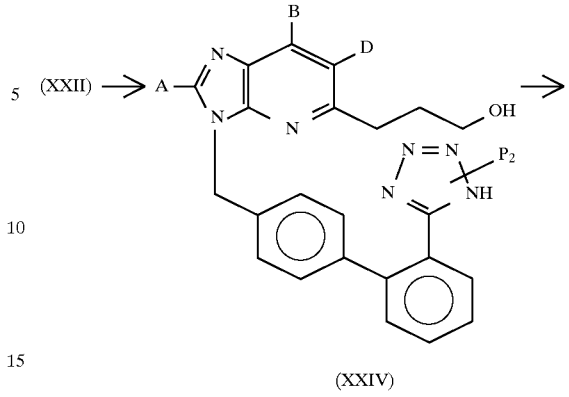

(XXIV)

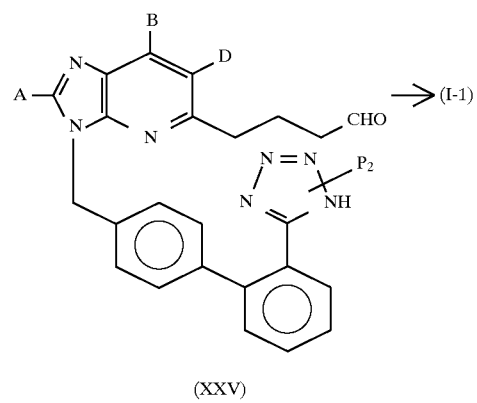

(XXV)

wherein A, B, D and $P_2$ are the same as defined previously.

The present invention also provides pharmacologically acceptable salts of the compounds of formula(I) which may be prepared by a conventional method, and among them, sodium or potassium salts are preferred.

The novel substituted pyridyl imidazole derivatives and pharmacologically acceptable salts of the present invention have an antihypertensive activity due to the antagonistic action against angiotensin II, and, therefore, they are useful for the treatment of acute or chronic cardiac defficiencies and various renal disorders as well as hypertension.

The compounds of the present invention may be also useful for the treatment of migraine, Raynaud's disease and various ocular diseases caused by elevated intraocular pressure and for the prevention of the progress of atherosclerosis. The compounds may be used separately or together with other antihypertensive agents such as a diuretic, an angiotensin converting enzyme inhibitor, a calcium-channel blocker, a potassium-channel blocker and the like.

Accordingly, the present invention also provides pharmaceutical compositions containing the compounds of formula (I) and pharmaceutically acceptable salts thereof as active ingredients and pharmacologically acceptable carriers.

The pharmaceutical compositions of the present invention may be administered orally or by injection. The pharmaceutical composition in a unit dosage may comprise about 0.1 to 1000 mg, more preferably 1 to 500 mg of the active ingredient, and be administrated 4 times or less, more preferably once or twice per day for an adult depending on the age and body weight of the patient, the nature and severity of the illness, and so on. The compositions of the present invention may comprise conventional adjuvants such as filler, anti-coagulant, binder, lubricant and flavoring agent. The formulation may be carried out in accordance with a conventional method.

Exemplary compounds of formula(I) of the present invention are as follows:

I-1. 2-butyl-5-dimethoxymethyl-6-phenyl-3-[2'-(1H-tetrazol-5-yl)-biphenyl-4-ylmethyl]-3H-imidazo[4,5-b]pyridine;

I-2. 2-butyl-5-diethoxymethyl-6-phenyl-3-[2'-(1H-tetrazol-5-yl)-biphenyl-4-ylmethyl]-3H-imidazo[4,5-b]pyridine;

I-3. 2-butyl-5-(1,3-dioxolan-2-yl)-6-phenyl-3-[2'-(1H-tetrazol-5-yl)-biphenyl-4-ylmethyl]-3H-imidazo[4,5-b]pyridine;

I-4. 2-butyl-5-(1,3-dioxan-2-yl)-6-phenyl-3-[2'-(1H-tetrazol-5-yl)-biphenyl-4-ylmethyl]-3H-imidazo[4,5-b]pyridine;

I-5. 2-butyl-5-dimethoxymethyl-6-(4-hydroxymethylphenyl-1-yl)-3-[2'-(1H-tetrazol-5-yl)-biphenyl-4-ylmethyl]-3H-imidazo[4,5-b]pyridine;

I-6. 2-butyl-5-dimethoxymethyl-6-(4-benzyloxymethylphenyl-1-yl)-3-[2'-(1H-tetrazol-5-yl)-biphenyl-4-ylmethyl]-3H-imidazo[4,5-b]pyridine;

I-7. 2-butyl-5-dimethoxymethyl-6-(2-methoxyphenyl-1-yl)-3-[2'-(1H-tetrazol-5-yl)-biphenyl-4-ylmethyl]-3H-imidazo[4,5-b]pyridine;

I-8. 2-butyl-5-dimethoxymethyl-6-(4-methoxyphenyl-1-yl)-3-[2'-(1H-tetrazol-5-yl)-biphenyl-4-ylmethyl]-3H-imidazo[4,5-b]pyridine;

I-9. 2-butyl-5-dimethoxymethyl-6-(2-nitrophenyl-1-yl)-3-[2'-(1H-tetrazol-5-yl)-biphenyl-4-ylmethyl]-3H-imidazo[4,5-b]pyridine;

I-10. 2-butyl-5-dimethoxymethyl-6-(2-aminophenyl-1-yl)-3-[2'-(1H-tetrazol-5-yl)-biphenyl-4-ylmethyl]-3H-imidazo[4, 5-b]pyridine;

I-11. 2-butyl-5-dimethoxymethyl-6-(2-phenylethyl-1-yl)-3-[2'-(1H-tetrazol-5-yl)-biphenyl-4-ylmethyl]-3H-imidazo[4,5-b]pyridine;

I-12. 2-butyl-5-dimethoxymethyl-6-benzyl-3-[2'-(1H-tetrazol-5-yl)-biphenyl-4-ylmethyl]-3H-imidazo[4,5-b]pyridine;

I-13. 2-butyl-5-dimethoxymethyl-6-(pyridin-2-yl)-3-[2'-(1H-tetrazol-5-yl)-biphenyl-4-ylmethyl]-3H-imidazo[4,5-b]pyridine;

I-14. 2-butyl-5-dimethoxymethyl-6-(pyridin-3-yl)-3-[2'-(1H-tetrazol-5-yl)-biphenyl-4-ylmethyl]-3H-imidazo[4,5-b]pyridine;

I-15. 2-butyl-5-dimethoxymethyl-6-(pyridin-4-yl)-3-[2'-(1H-tetrazol-5-yl)-biphenyl-4-ylmethyl]-3H-imidazo[4,5-b]pyridine;

I-16. 2-butyl-5-dimethoxymethyl-6-(1-oxopyridin-2-yl)-3-[2'-(1H-tetrazol-5-yl)-biphenyl-4-ylmethyl]-3H-imidazo[4,5-b]pyridine;

I-17. 2-butyl-5-dimethoxymethyl-6-(1-oxopyridin-3-yl)-3-[2'-(1H-tetrazol-5-yl)-biphenyl-4-ylmethyl]-3H-imidazo[4,5-b]pyridine;

I-18. 2-butyl-5-dimethoxymethyl-6-(1-oxopyridin-4-yl)-3-[2'-(1H-tetrazol-5-yl)-biphenyl-4-ylmethyl]-3H-imidazo[4,5-b]pyridine;

I-19. 2-butyl-5-diethoxymethyl-6-(pyridin-2-yl)-3-[2'-(1H-tetrazol-5-yl)-biphenyl-4-ylmethyl]-3H-imidazo[4,5-b]pyridine;

I-20. 2-butyl-5-(1,3-dioxolan-2-yl)-6-(pyridin-2-yl)-3-[2'-(1H-tetrazol-5-yl)-biphenyl-4-ylmethyl]-3H-imidazo[4,5-b]pyridine;

I-21. 2-butyl-5-(1,3-dioxan-2-yl)-6-(pyridin-2-yl)-3-[2'-(1H-tetrazol-5-yl)-biphenyl-4-ylmethyl]-3H-imidazo[4,5-b]pyridine;

I-22. 2-butyl-5-diethoxymethyl-6-(pyridin-3-yl)-3-[2'-(1H-tetrazol-5-yl)-biphenyl-4-ylmethyl]-3H-imidazo[4,5-b]pyridine;

I-23. 2-butyl-5-(1,3-dioxolan-2-yl)-6-(pyridin-3-yl)-3-[2'-(1H-tetrazol-5-yl)-biphenyl-4-ylmethyl]-3H-imidazo[4,5-b]pyridine;

I-24. 2-butyl-5-(1,3-dioxan-2-yl)-6-(pyridin-3-yl)-3-[2'-(1H-tetrazol-5-yl)-biphenyl-4-ylmethyl]-3H-imidazo[4,5-b]pyridine;

I-25. 2-butyl-5-diethoxymethyl-6-(pyridin-4-yl)-3-[2'-(1H-tetrazol-5-yl)-biphenyl-4-ylmethyl]-3H-imidazo[4,5-b]pyridine;

I-26. 2-butyl-5-(1,3-dioxolan-2-yl)-6-(pyridin-4-yl)-3-[2'-(1H-tetrazol-5-yl)-biphenyl-4-ylmethyl]-3H-imidazo[4,5-b]pyridine;

I-27. 2-butyl-5-(1,3-dioxan-2-yl)-6-(pyridin-4-yl)-3-[2'-(1H-tetrazol-5-yl)-biphenyl-4-ylmethyl]-3H-imidazo[4,5-b]pyridine;

I-28. 2-ethoxy-5-dimethoxymethyl-6-phenyl-3-[2'-(1H-tetrazol-5-yl)-biphenyl-4-ylmethyl]-3H-imidazo[4,5-b]pyridine;

I-29. 2-ethoxy-5-dimethoxymethyl-6-(pyridin-2-yl)-3-[2'-(1H-tetrazol-5-yl)-biphenyl-4-ylmethyl)-3H-imidazo[4,5-b]pyridine;

I-30. 2-ethoxy-5-dimethoxymethyl-6-(1-oxopyridin-4-yl)-3-[2'-(1H-tetrazol-5-yl)-biphenyl-4-ylmethyl]-3H-imidazo[4,5-b]pyridine;

I-31. 2-butyl-5-dimethoxymethyl-3-[2'-(1H-tetrazol-5-yl)-biphenyl-4-ylmethyl]-3H-imidazo[4,5-b]pyridine;

I-32. 2-butyl-5-dimethoxymethyl-6-bromo-3-[2'-(1H-tetrazol-5-yl)-biphenyl-4-ylmethyl]-3H-imidazo[4,5-b]pyridine;

I-33. 2-butyl-5-dimethoxymethyl-6-phenyl-7-methyl-3-[2'-(1H-tetrazol-5-yl)-biphenyl-4-ylmethyl]-3H-imidazo[4,5-b]pyridine;

I-34. 2-butyl-5-dimethoxymethyl-6-(pyridin-2-yl)-7-methyl-3-20 [2'-(1H-tetrazol-5-yl)-biphenyl-4-ylmethyl]-3H-imidazo[4,5-b]pyridine;

I-35. 2-butyl-5-methyl-6-phenyl-7-dimethoxymethyl-3-[2'-(1H-tetrazol-5-yl)-biphenyl-4-ylmethyl]-3H-imidazo[4,5-b]pyridine; and I-36. 2-butyl-5-dimethoxymethyl-6-[2-(ethoxycarbonyl)-ethyl-1-yl]-3-[2'-(1H-tetrazol-5-yl)-biphenyl-4-ylmethyl]-3H-imidazo[4,5-b]pyridine.

The following Examples are intended to illustrate the present invention more specifically, without limiting the scope of the invention. The percentages as used in the Examples are by v/v, unless otherwise specified.

EXAMPLE 1

Preparation of 2-butyl-5-dimethoxymethyl-6-phenyl-3-[2'-(1H-tetrazol-5-yl)biphenyl-4-ylmethyl]-3H-imidazo[4,5-b]pyridine Step 1: Preparation of 6-amino-3-bromo-2-picoline 32.4 g(0.3 mole) of 6-aminopicoline was dissolved in a mixture of 28 g of conc. sulfuric acid and 120 ml of water and the resulting solution was cooled in ice water. 52.8 g(0.33 mole) of bromine was added dropwise to the solution over 30 minutes at 0° C. The reaction solution was stirred for 20 minutes at room temperature and neutralized with cold aqueous NaOH solution. The resultant was filtered and purified by column chromatography using methylene chloride and ethyl acetate as an eluent to obtain 31 g of the title compound(yield 55%).

Step 2: Preparation of 3-bromo-5-nitro-6-amino-2-picoline 20 g(0.107 mole) of the compound obtained in step 1 was dissolved in 110 ml of conc. sulfuric acid and thereto was added dropwise 9.4 ml(0.12 mole) of nitric acid for 30 minutes at 0° C. The reaction solution was stirred for 1 hour at 0° C. and, subsequently stirred for another 1 hour at room temperature. The resultant was neutralized with cold 40% aqueous NaOH solution and filtered to get a yellow solid. The solid was washed with distilled water(100 ml×3) and dried in a vacuum oven at 60° C. for 24 hours to obtain 23.8 g of the title compound(yield 96%).

Step 3: Preparation of 3-bromo-5,6-diamino-2-picoline 7.7 g(0.0332 mole) of the compound obtained in step 2 was dissolved in a mixture of 27 ml of ethanol and 7 ml of water and to the resulting solution were added 20 g(0.36 mole) of iron powder and 0.33 ml of conc. hydrochloric acid. The resultant was refluxed with stirring for 1 hour, filtered through Cellite to remove the remaining iron powder and washed with ethanol(50 ml×3). The filtrate was concentrated under reduced pressure and dissolved in ethyl acetate. The resultant was passed through silica gel and concentrated under reduced pressure to obtain 6.6 g of the title compound(yield 98%).

Step 4: Preparation of 3-bromo-2-butyl-5-methyl-1H-imidazo[4,5-b]pyridine 9.0 g(0.0446 mole) of the compound obtained in step 3 and 5.5 g(0.058 mole) of valeric acid were mixed with 30 ml of polyphosphoric acid and stirred 3 hours at 110° C. The reaction solution was dissolved in a mixture of 50 ml of cold water and 50 ml of THF and the resulting solution was neutralized to pH 8 with cold aqueous 40% NaOH solution with stirring vigorously and extracted with ethyl acetate(50 ml×3). Thereafter, the organic layer was dried over $Na_2SO_4$, concentrated under reduced pressure and recrystallized from hexane-methylene chloride to obtain 9.8 g of the title compound(yield 82%).

Step 5: Preparation of 6-bromo-2-butyl-5-methyl-1H-imidazo[4,5-b]pyridine-4-oxide 7.8 g(0.0291 mole) of the compound obtained in step 4 was dissolved in 50 ml of methylene chloride and to the resulting solution was added 8.8 g(0.0436 mole) of 85% m-chloroperbenzoic acid. The resultant was stirred for 16 hours at room temperature and filtered to get solids, which were washed with ethyl ether(12 ml×3) to obtain 8.0 g of the title compound(yield 97%).

Step 6: Preparation of 6-bromo-2-butyl-5-hydroxymethyl-1H-imidazo[4,5-b]pyridine 8.0 g (0.02817 mole) of the compound obtained in step 5 was dissolved in 20 ml of anhydrous acetic acid. The resulting solution was stirred for 1 hour at 120° C., and evaporated under reduced pressure to remove anhydrous acetic acid. Thereafter, the residue was dissolved in a mixture of 30 ml of methanol and 40 ml of 3N LiOH. The resulting solution was refluxed for 1 hour, evaporated under reduced pressure to remove methanol, neutralized with 1N HCl and extracted with ethyl acetate(50 ml×3). The organic layer was dried over $Na_2SO_4$. The residue was concentrated under reduced pressure and purified with column chromatography(hexane:ethyl acetate =1:2) to obtain 5.3 g of the title compound(yield 66%).

Step 7: Preparation of 6-bromo-2-butyl-5-hydroxymethyl-3-(2-oxo-2-phenylethyl)-3H-imidazo(4,5-b]pyridine 10 g(0.0352 mole) of the compound obtained in step 6, 7.59 g(0.0387 mole) of 2-bromoacetophenone and 9.8 g(0.0704 mole) of $K_2CO_3$ were dissolved in 50 ml of dimethyl formamide. The reaction solution was stirred for 3 hours at room temperature, diluted with 200 ml of ethyl acetate and washed with water(100 ml×3). The organic layer was dried over $Na_2SO_4$ and purified with column chromatography(silica gel, methylene chloride:ethyl acetate =1:1) to obtain 6.96 g of the title compound(yield 64%).

Step 8: Preparation of 2-butyl-5-hydroxymethyl-3-(2-oxo-2-phenylethyl)-6-phenyl-3H-imidazo[4,5-b]pyridine 4.8 g(0.01197 mole) of the compound obtained in step 7, 3.75 g(0.03591 mole) of phenylboric acid, 0.2 g(0.0012 mole) of palladium acetate, 0.46 g(0.0024 mole) of triphenylphosphine and 8.9 ml(0.0838 mole) of triethylamine were dissolved in 20 ml of dimethyl formamide. The reaction solution was stirred for 3 hours at 120° C., diluted with 100 ml of ethyl acetate and washed with water(50 ml×3). The organic layer was dried over $Na_2SO_4$ and concentrated under reduced pressure. The residue was purified with column chromatography(5% MeOH in $CH_2Cl_2$) to obtain 4.57 g of the title compound(yield 96%).

Step 9: Preparation of 2-butyl-5-hydroxymethyl-6-phenyl-3H-imidazo[4,5-b]pyridine 4 g(0.010 mole) of the compound obtained in step 8 was dissolved in a mixture of 40 ml of acetic acid and 40 ml of methanol and to the resulting solution was added 13.1 g(0.0002 mole) of zinc powder. The resultant was stirred under ultrasonification for 4 hours, filtered and washed with acetic acid(10 ml×3). To the filtrate was added 50 ml of saturated aqueous ethylene diamine tetraacetic acid solution and then the resultant was stirred for 10 minutes. After adding 100 ml of ethyl acetate, the solution was filtered and washed with 100 ml of aqueous 10% $NaHCO_3$ solution. The organic layer was dried over $Na_2SO_4$ and concentrated under reduced pressure. The residue was purified with column chromatography($CH_2Cl_2 \rightarrow$ 10% MeOH/$CH_2Cl_2$) to obtain 2.4 g of the title compound(yield 86%).

Step 10: Preparation of 2-butyl-3-{2'-[1-(1-ethoxyethyl)-1H-tetrazol-5-yl]-biphenyl-4-ylmethyl}-5-hydroxymethyl-6-phenyl-3H-imidazo[4,5-b]pyridine 2.1 g(0.0075 mole) of the compound obtained in step 9 and 3.6 g(0.009 mole) of 2'-[1-(1-ethoxyethyl)-1H-tetrazol-5-yl]-biphenyl-4-ylmethyl bromide were dissolved in 20 ml of dimethyl formamide and to the resulting solution was added 2.1 g(0.015 mole) of $K_2CO_3$. The resultant was stirred for 5 hours at room temperature and diluted with 100 ml of ethyl acetate, and washed with water(50 ml×3). The organic layer was dried over $Na_2SO_4$, concentrated under reduced pressure and purified with column chromatography(5% MeOH/$CH_2Cl_2$) to obtain 2.85 g of the title compound(yield 65%).

Step 11: Preparation of 2-butyl-3-{2'-[1-(1-ethoxyethyl)-1H-tetrazol-5-yl]-biphenyl-4-ylmethyl}-5-formyl-6-phenyl-3H-imidazo[4,5-b]pyridine 0.6 g(0.001 mole) of the compound obtained in step 10 was dissolved in 10 ml of $CH_2Cl_2$ and to the resulting solution was added 1.76 g(0.02 mole) of activated $MnO_2$. The resultant was stirred for 16 hours at room temperature and filtered through Cellite with washing with 5% MeOH/ $CH_2Cl_2$(10 ml×4). The filtrate was concentrated under reduced pressure to obtain 0.52 g of the title compound(yield 87%).

Step 12: Preparation of 2-butyl-5-dimethoxymethyl-6-phenyl-3-[2'-(1H-tetrazol-5-yl)-biphenyl-4-ylmethyl]-3H-imidazo[4,5-b ]pyridine 0.1 g(0.000169 mole) of the compound obtained in step 11 and 0.36 g(0.00338 mole) of trimethylformate were dissolved in 5 ml of methanol and to the resulting solution was added 0.5 ml of 3% anhydrous HCl/MeOH. The resultant was refluxed for 2 hours and cooled. 5 ml of saturated $NaHCO_3$ solution was added to the reaction solution. The resulting solution was evaporated under reduced pressure to remove methanol and thereafter extracted with ethyl acetate(5 ml×4). The organic layer was dried over $Na_2SO_4$ and concentrated under reduced pressure. The residue was recrystallized from hexane-methylene chloride to obtain 75 mg of the title compound in a white solid form(yield 79.4%).

¹H NMR(300 MHz, CDCl₃)δ0.84(t, 3 H), 1.3(m, 2 H), 1.72(m, 2H). 2.74(t, 2H), 3.16(s, 3H), 5.14(s, 1H), 5.46(s, 2H), 6.75(d, 2H), 5.88(d, 2H), 7.15(m, 1H), 7.23~7.44(m, 7H), 7.77(d, 1H), 7.87(s, 1H).

EXAMPLE 2

Preparation of 2-butyl-5-diethoxymethyl-6-phenyl-3-[2'-(1H-tetrazol-5-yl)-biphenyl-4-ylmethyl]-3H-imidazo[4,5-b]pyridine 0.1 g(0.000169 mole) of the aldehyde compound obtained in step 11 of Example 1 was dissolved in 5 ml of ethanol and to the resulting solution was added 0.5 ml of 3% anhydrous HCl/EtOH. The resultant was refluxed for 4 hours and purified as the same method as in step 12 of Example 1 to obtain 95 mg of the title compound(yield 96%).

¹H NMR(300 MHz, CDCl₃,)δ0.84(t, 3H), 0.92(t, 6H), 1.32(m, 2H), 1.72(s, 1H), 2.74(t, 2H), 3.28(m, 2H), 3.54(m, 2H), 5.31(s, 1H), 5.51(s, 2H), 6.75(d, 2H), 6.91(d, 2H), 7.24~7.43(m, 7H), 7.76(d, 1H), 7.87(s, 1H). cl EXAMPLE 3

Preparation of 2-butyl-5-(1,3-dioxolan-2-yl)-6-phenyl-3-[2'-(1H-tetrazol-5-yl)-biphenyl-4-ylmethyl]-3H-imidazo[4,5-b]pyridine 0.1 g(0.000169 mole) of the aldehyde compound obtained in step 11 of Example 1 and 0.032 g(0.000507 mole) of ethylene glycol were dissolved in 5 ml of benzene and to the resulting solution was added 0.01 mg of p-toluenesulfonic acid. The resultant was refluxed for 6 hours and thereto were added 1 ml of aqueous saturated NaHCO₃ solution and 5 ml of water. The reaction solution was extracted with ethyl acetate(5 ml×3) and the organic layer was dried over Na₂SO₄ and concentrated under reduced pressure. The resultant was recrystallized from hexane-methylene chloride to obtain 80 mg of the title compound(yield 85%).

¹H NMR(300 MHz, CDCl₃)δ0.79(t, 3H), 1.25(m, 2H), 1.65(m, 2H), 2.64(t, 2H), 3.68(m, 2H), 4.00(m, 2H), 5.27(s, 2H), 5.82(s, 1H), 6.81(m, 4H), 7.19~7.37(m,7H), 7.63(d, 1H), 7.78(s,1H).

EXAMPLE 4

Preparation of 2-butyl-5-(1,3-dioxan-2-yl)-6-phenyl-3-[2'-(1-tetrazol-5-yl)-biphenyl-4-ylmethyl]-3H-imidazo[4,5-b]pyridine The same procedure as in Example 3 was repeated using 0.1 g(0.000169 mole) of the aldehyde compound obtained in step 11 of Example 1 and 0.039(0.0005 mole) of 1,3-propanediol to obtain 0.085 g of the title compound(yield 96%).

¹H NMR(300 MHz. CDCl₃)δ0.80(t, 3H), 1.26(m, 2H), 1.69(m, 2H), 2.66(t, 2H), 3.57(m, 2H), 3.76(t, 2H), 4.02(m, 2H), 5.37(s, 2H), 5.41(s, 1H), 6.72(d,2H), 6.86(d,2H), 7.19~7.44(m,7H), 7.75(d,1H), 7.89(s,1H).

EXAMPLE 5

Preparation of 2-butyl-5-(1,3-dithiolan-2-yl)-6-phenyl-3-[2'-(1H-tetrazol-5-yl)-biphenyl-4-ylmethyl]-3H-imidazo[4,5-b]pyridine 0.1 g(0.000169 mole) of the aldehyde compound obtained in step 11 of Example 1 and 0.024 g(0.00025 mole) of 1,2-ethanedithiol were dissolved in 5 ml of benzene and to the resulting solution was added 0.01 mg of p-toluenesulfonic acid. The resultant was refluxed for 6 hours, neutralized with aqueous NaHCO₃ solution and extracted with ethyl acetate(5 ml×3). The organic layer was dried over Na₂SO₄, concentrated under reduced pressure and evaporated under reduced pressure (1 mmHg, 80° C.) for 5 hours to remove the residual 1,2-ethanedithiol. The resultant was recrystallized from hexane-methylene chloride to obtain 80 mg of the title compound(yield 84%).

¹H NMR(300 MHz, CDCl₃)δ0.70(t, 3H), 1.16(m, 2H), 1.54(m, 2H), 2.56(t, 2H), 3.03(m, 2H), 3.49(m, 2H), 5.16(s, 2H), 5.64(s, 1H), 6.80(d, 2H), 6.92(d, 2H), 7.09~7.47(m, 9H), 7.65(s, 1H).

EXAMPLE 6

Preparation of 2-butyl-5-dimethoxymethyl-6-(4-methoxyphenyl-1-yl)-3-[2'-(1H-tetrazol-5-yl)-biphenyl-4-ylmethyl]-3H-imidazo[4,5-b]pyridine The same procedures as in steps 8 to 12 of Example 1 were repeated using 1 g(0.00249 mole) of the compound obtained in step 7 of Example 1 and 0.76 g(0.00498 mole) of 4-methoxyphenylboric acid to obtain 0.18 g of the title compound(yield 12%).

¹H NMR(300 MHz. CD₃OD)δ0.92(t, 3H), 1.36(m, 2H), 1.72(m, 2H), 2.89 (t, 2H), 3.31(s, 6H), 3.87(s, 3H), 5.29(s, 1H), 5.65(s, 1H), 7.03(d, 2H), 7.06(d, 2H), 7.15 (d, 2H), 7.34(d, 2H), 7.43~7.59(m, 4H), 7.81(s, 1H).

EXAMPLE 7

Preparation of 2-butyl-5-dimethoxymethyl-6-bromo-3-[2'-(1H-tetrazol-5-yl)-biphenyl-4-ylmethyl]-3H-imidazo[4,5-b]pyridine The same procedures as in steps 10 to 12 of Example 1 were repeated using 0.3 g(0.00106 mole) of the compound obtained in step 6 of Example 1 to obtain 0.044 g of the title compound.

¹H NMR(200 MHz, CD₃OD)δ0.9(t, 3H), 1.4(m, 2H), 1.7(m, 2H), 2.85(t, 2H), 3.5(s, 6H), 5.6(s, 2H), 5.8(s, 1H), 7.15(m, 4H), 7.6(m, 4H), 8.2(s, 1H).

EXAMPLE 8

Preparation of 2-butyl-5-dimethoxymethyl-6-(pyridin-2-yl)-3-[2'-(1H-tetrazol-5-yl)-biphenyl-4-ylmethyl]-3H-imidazo[4,5-b]pyridine Step 1: Preparation of 2-butyl-5-hydroxymethyl-6-(pyridine-2-yl)-3-(2-oxo-2-phenylethyl)-3H-imidazo[4,5-b]pyridine 1 g(0.00249 mole) of the compound obtained in step 7 of Example 1 was dissolved in 10 ml of toluene and to the resulting solution were 1 g(0.00274 mole) of 2-tributyltin pyridine and 0.058 g(0.00005 mole) of tetrakistriphenyl-phosphine palladium. The resultant was refluxed for 24 hours, and cooled to room temperature after the completion of the reaction. The reaction solution was extracted with 100 ml of ethyl acetate and washed with 100 ml of water. The organic layer was dried over MgSO₄, filtered and concentrated under reduced pressure, and the residue was purified with column chromatography (ethyl acetate) to obtain 0.705 g of the title compound(yield 71%).

Step 2: Preparation of 2-butyl-5-dimethoxymethyl-6-(pyridin-2-yl)-3-[2'-(1H-tetrazol-5-yl)-biphenyl-4-ylmethyl]-3H-imidazo[4,5-b]pyridine The same procedures as in steps 9 to 12 of Example 1 were repeated using 0.7 g(0.00175 mole) of the compound obtained in the above step 1 to obtain 0.02 g of the title compound.

¹H NMR(300 MHz, CDCl₃)δ0.84(t, 3H), 1.33(m, 2H), 1.70(m, 2H), 2.76(t, 2H), 3.16(s, 3H), 5.20(s, 1H), 5.56(s, 2H), 6.82(d, 2H), 6.98(d, 2H), 7.15~8.5(m, 9H).

EXAMPLE 9

Preparation of 2-butyl-5-dimethoxymethyl-6-(4-fluorophenyl-1-yl)-3-[2'-(1H-tetrazol-5-yl)-biphenyl-4-ylmethyl]-3H-imidazo[4,5-b]pyridine The same procedures as in steps 8 to 12 of Example 1 were repeated using 0.5 g(0.00124 mole) of the compound obtained in step 7 of Example 1 and 4-fluorophenylboric acid to obtain 0.042 g of the title compound.

¹H NMR(200 MHz, CD₃OD)δ0.95(t, 3H), 1.4(m, 2H), 1.8(m, 2H), 2.95(t, 2H), 3.3(s, 6H), 5.25(s, 1H), 5.5(s, 2H), 7.0(d, 1H), 7.2(m, 5H), 7.4(m, 6H), 7.7(s, 1H).

EXAMPLE 10

Preparation of 2-butyl-5-dimethoxymethyl-3-[2'-(1H-tetrazol-5-yl)-biphenyl-4-ylmethyl]-3H-imidazo[4,5-b]pyridine Step 1: Preparation of 2-butyl-5-hydroxymethyl-1H-imidazo[4,5-b]pyridine 0.25 g(0.00088 mole) of 6-bromo-2-butyl-5-hydroxymethyl-1H-imidazo[4,5-b]pyridine obtained in step 6 of Example 1 was dissolved in 10 ml of ethanol and to the resulting solution was added 0.03 g of 10% palladium/activated carbon. The resultant was reacted at room temperature for 3 hours under about 3 atm of hydrogen using a hydrogenation apparatus. The reaction solution was filtered through Cellite with washing with 10% methanol/ethyl acetate(10 ml×3) and concentrated under reduced pressure to obtain 0.167 g of the title compound(yield 93%).

Step 2: Preparation of 2-butyl-5-dimethoxymethyl-3-[2'-(1H-tetrazol-5-yl)-biphenyl-4-ylmethyl]-3H-imidazo[4,5-b]pyridine The same procedures as in steps 10 to 12 of Example 1 were repeated using 0.15 g(0.00073 mole) of the compound obtained in the above step 1 to obtain 0.116 g of the title compound.

¹H NMR(200 MHz, CDCl₃)δ0.85(t, 3H), 1.30(m, 2H), 1.69(m, 2H), 2.65(t, 2H), 3.36(s, 6H), 5.41(d, 3H), 6.88(d, 2H), 6.98(d, 2H), 7.33~7.68 (m, 5H), 7.91(d, 1H).

EXAMPLE 11

Preparation of 2-butyl-5-dimethoxymethyl-7-methyl-3-[2'-(1H-tetrazol-5-yl)-biphenyl-4-ylmethyl]-3H-imidazo[4,5-b]pyridine Step 1: Preparation of 2-amino-3-nitro-4,6-dimethylpyridine 6.0 g(0.04911 mole) of 2-amino-4,6-dimethyl pyridine was dissolved in 20 ml of conc. sulfuric acid. The reaction solution was cooled to 0° C. in an ice bath and thereto was added dropwise 2.3 ml(0.04911 mole) of conc. nitric acid diluted with 5 ml of conc. sulfuric acid over 10 minutes. The resultant was stirred for 30 minutes at 0° C. and then added into ice water slowly to terminate the reaction. The reaction solution was neutralized to pH 7-8 with 20% aqueous sodium hydroxide solution and extracted with ethyl acetate (100 ml×3). The organic layer was dried over sodium sulfate anhydride and concentrated under reduced pressure. The residue was recrystallized from methanol-ethyl acetate to obtain 4.26 g of the title compound as a yellow solid(yield 52%).

Step 2: Preparation of 2,3-diamino-4,6-dimethylpyridine 4.2 g(0.02515 mole) of the compound obtained in the above step 1 was dissolved in 50 ml of ethanol and to the resulting solution was added 0.42 g of 10% palladium/activated carbon. The resultant was reacted for 3 hours under about 3-4 atm of hydrogen using a hydrogenation apparatus. The reaction solution was filtered through Cellite and washed with 10% methanol/ethyl acetate(20 ml×3). The filtrate was concentrated under reduced pressure to obtain 3.2 g of the title compound(yield 93%).

Step 3: Preparation of 2-butyl-5,7-dimethyl-1H-imidazo[4,5-b]pyridine

The same procedure as in step 4 of Example 1 was repeated using 2.5 g(0.01825 mole) of the diamine compound obtained in the above step 2. The resultant was purified with column chromatography (hexane/ethyl acetate=1:1) to obtain 3.0 g of the title compound(yield 81%).

Step 4: Preparation of 2-butyl-5,7-dimethyl-1H-imidazo[4,5-b]pyridine-4-oxide

The same procedure as in step 5 of Example 1 was repeated using 3.0 g(0.01478 mole) of the compound obtained in the above step 3 to obtain 2.97 g of the title compound as a white solid(yield 92%).

Step 5: Preparation of 2-butyl-5-hydroxymethyl-7-methyl-1H-imidazo[4,5-b]pyridine The same procedure as in step 6 of Example 1 was repeated using 2.8 g(0.01278 mole) of the compound obtained in the above step 4. The resultant was purified with column chromatography (ethyl acetate) to obtain 1.87 g of the title compound as a white solid(yield 67%).

Step 6: Preparation of 2-butyl-5-dimethoxymethyl-7-methyl-3-[2'-(1H-tetrazol-5-yl)-biphenyl-4-ylmethyl]-3H-imidazo[4,5-b]pyridine The same procedures as in steps 10 to 12 of Example 1 were repeated using 1.2 (0.00548 mole) of the compound obtained in step 5 to obtain 0.57 g of the title compound.

¹H NMR(200 MHz, CDCl₃)δ0.86(t, 3H), 1.30(m, 2H), 1.65(m, 2H), 2.53(t, 2H), 2.58(s, 3H), 3.27(s, 6H), 5.42(s, 2H), 5.68(s, 1H), 6.94(d, 2H), 7.05(d, 2H), 7.2~7.6(m, 4H), 7.94(m, 1H).

EXAMPLE 12

Preparation of 2-ethyl-5-dimethoxymethyl-7-methyl-3-[2'-(1H-tetrazol-5-yl)-biphenyl-4-ylmethyl]-3H-imidazo[4,5-b]pyridine Step 1: Preparation of 2-ethyl-5-hydroxymethyl-7-methyl-1H-imidazo[4,5-b]pyridine The same procedures as in steps 4 to 6 of Example 1 were repeated using 3.0 g(0.02190 mole) of the compound obtained in step 2 of Example 11 and 2.1 ml(0.002847 mole) of propionic acid. The resultant was purified with column chromatography (10% methanol/ethyl acetate) to obtain 1.50 g of the title compound as a light yellow solid.

Step 2: Preparation of 2-ethyl-5-dimethoxymethyl-7-methyl-3-[2'-(1H-tetrazol-5-yl)-biphenyl-4-ylmethyl]-3H-imidazo[4,5-b]pyridine The same procedures as in steps 10 to 12 of Example 1 were repeated using 1.2 g(0.00628 mole) of the compound obtained in the above step 1 to obtain 1.02 g of the title compound as a white solid.

¹H NMR(200 MHz, CDCl₃)δ1.22(t, 3H), 2.62(s,3H), 2.70 (m, 2H), 3.31(s, 6H), 5.43(s, 2H), 5.80(s, 1H), 6.98~7.60(m, 8H), 7.95(d, 1H).

EXAMPLE 13

Preparation of 2-butyl-5-dimethoxymethyl-6-[2-(ethoxycarbonyl)-ethyl-1-yl]-3-[2'-(1H-tetrazol-5-yl)-biphenyl-4-ylmethyl]-3H-imidazo[4,5-b]pyridine Step 1: Preparation of 2-butyl-5-hydroxymethyl-3-(2-oxo-2-phenylethyl)-6-styryl-3H-imidazo[4,5-b]pyridine 5.08 g(0.0127 mole) of the compound obtained in step 7 of Example 1 was dissolved in 12 ml of dimethylformamide (DMF) and to the resulting solution were added 5.64 g(0.0381 mole) of styrylboric acid, 0.29 g(0.00127 mole) of palladium acetate, 0.67 g(0.00254 mole) of triphenylphosphine and 13 ml(0.0889 mole) of triethylamine. The resultant was stirred for 1 hour at 120° C., cooled, extracted with 300 ml of ethyl acetate and washed with 300 ml of water. The organic layer was dried over anhydrous magnesium sulfate, concentrated under reduced pressure and purified with column chromatography (methanol/methylene chloride=1:9) to obtain 4.58 g of the title compound(yield 85%).

Step 2: Preparation of 2-butyl-5-hydroxymethyl-6-styryl-3H-imidazo[4,5-b]pyridine 2.12 g(0.005 mole) of the compound obtained in the above step 1 was dissolved in a mixture of 30 ml of acetic acid and 30 ml of methanol and reacted with 6.5 g(0.1 mole) of zinc powder similarly to step 9 of Example 1 to obtain 0.765 g of the title compound(yield 50%).

Step 3: Preparation of 2-butyl-3-{2'-[1-(1-ethoxyethyl)-1H-tetrazol-5-yl]-biphenyl-4-ylmethyl}-5-hydroxymethyl-6-styryl-3H-imidazo[4,5-b]pyridine 0.7 g(0.00229 mole) of the compound obtained in the above step 2 was dissolved in 5 ml of DMF and reacted with 0.63 g(0.00458 mole) of $K_2CO_3$ and 1.16 g(0.00298 mole) of 2'-[1-(1-ethoxyethyl)-1H-tetrazol-5-yl]-biphenyl-4-ylmethylbromide similarly to step 10 of Example 1 to obtain 0.91 g of the title compound(yield 65%).

Step 4: Preparation of 2-butyl-3-{2'-[1-(1-ethoxyethyl)-1H-tetrazol-5-yl]-biphenyl-4-ylmethyl}-5-hydroxymethyl-6-formyl-3H-imidazo[4,5-b]pyridine 0.91 g(0.00148 mole) of the compound obtained in the above step 3 was dissolved in 10 ml of methylene chloride and passed ozone gas until the reaction solution turned into light blue, while keeping the temperature at −78° C. with a mixture of dry ice and acetone. The remaining ozone gas was removed by passing oxygen gas. To the resultant was added 1.1 ml](0.0148 mole) of methyl sulfide. The resulting solution was warmed to room temperature and stirred for about 1 hour. The resultant was concentrated under reduced pressure and purified with silica gel column chromatography (ethyl acetate) to obtain 0.4 g of the title compound(yield 50%).

Step 5: Preparation of 2-butyl-6-[2-(ethoxycarbonyl)-vinyl-1-yl]-3-{2'-[1-(1-ethoxyethyl)-1H-tetrazol-5-yl]-biphenyl-4-ylmethyl}-5-hydroxymethyl-3H-imidazo[4,5-b]pyridine 0.1 g(0.00018 mole) of the compound obtained in the above step 4 was dissolved in 5 ml of benzene and to the resulting solution was added 0.081 g(0.00022 mole, 95%) of (carboethoxy-methylene) triphenylphosphorane. The resultant was stirred for 1 hour at room temperature and concentrated under reduced pressure. The residue was purified with silica gel column chromatography (hexane:ethyl acetate =1:2) to obtain 0.103 g of the title compound(yield 94%).

Step 6: Preparation of 2-butyl-6-[2-(ethoxycarbonyl)-ethyl-1-yl]-3-{1'-[1-(1-ethoxyethyl)-1H-tetrazol-5-yl]-biphenyl-4-ylmethyl}-5-hydroxymethyl-3H-imidazo[4,5-b]pyridine 0.1 g(0.00016 mole) of the compound obtained in the above step 5 was dissolved in 5 ml of ethanol and to the resulting solution was added 0.01 g of 10% Pd/C. The resultant was stirred for 1 hour at room temperature under hydrogen(50 psi). The reaction solution was passed through Cellite with a thickness of 3 cm and concentrated under reduced pressure. The resultant was purified with silica gel column chromatography (hexane:ethyl acetate =1:1) to obtain 0.088 g of the title compound(yield 90%).

Step 7: Preparation of 2-butyl-6-[2-(ethoxycarbonyl)-ethyl-1-yl]-3-{2'-[1-(1-ethoxyethyl)-1H-tetrazol-5-yl]-biphenyl-4-ylmethyl}-5-formyl-3H-imidazo[4,5-b]pyridine 0.088 g(0.00014 mole) of the compound obtained in the above step 6 was dissolved in 5 ml of methylene chloride and to the resulting solution was added 0.24 mg(0.0028 mole) of $MnO_2$. The resultant was stirred for 24 hours at room temperature, passed through Cellite with a thickness of 3 cm and concentrated under reduced pressure. The residue was purified with silica gel column chromatography (hexane:ethyl acetate=1:1) to obtain 0.077 g of the title compound(yield 93%).

Step 8: Preparation of 2-butyl-5-dimethoxymethyl-6-[2-(ethoxycarbonyl)-ethyl-1-yl]-3-[2'-(1H-tetrazol-5-yl)-biphenyl-4-ylmethyl]-3H-imidazo[4,5-b]pyridine 0.077 g(0.00012 mole) of the aldehyde compound obtained in the above step 7 was dissolved in 3 ml of methanol and to the resulting solution was added 0.5 ml of 3% anhydrous HCl/methanol. The resultant was refluxed for 3 hours and purified similarly to step 12 of Example 1 to obtain 0.064 g of the title compound(yield 92%).

$^1$H NMR(200 MHz, $CDCl_3$)δ1.82(t, 3H), 1.26(s,5H), 1.65 (m, 2H), 2.57(m, 4H), 3.12(t, 2H), 3.38(s, 6H), 4.15(q, 2H), 5.37(s, 2H), 5.41(s, 1H), 6.88(q, 4H), 7.30(m, 2H), 7.65(m, 2H), 7.93(d, 1H).

EXAMPLE 14

Preparation of 2-butyl-5-dimethoxymethyl-6-(thiophen-2-yl)-3-[2'-(1H-tetrazol-5-yl)-biphenyl-4-ylmethyl]-3H-imidazo[4,5-b]pyridine 5 The same procedures as in steps 8 to 12 of Example 1 were repeated using 0.3 g(0.00075 mole) of the compound obtained in step 7 of Example 1 and 0.24 g(0.00188 mole) of 2-thiophenyl-boric acid to obtain 0.070 g of the title compound.

$^1$H NMR(300 MHz, $CDCl_3$)δ0.83(t, 3H), 1.30(m, 2H), 1.7(m, 2H), 2.72(t, 2H), 3.19(s, 6H), 5.31(s, 1H), 5.44(s, 2H), 6.73(d, 2H), 6.89(d, 2H), 7.06~7.41(m, 6H), 7.73(d, 1H).

EXAMPLE 15

Preparation of 2-butyl-5-dimethoxymethyl-6-(2-phenylethyl-1-yl)-3-[2'-(1H-tetrazol-5-yl)-biphenyl-4-ylmethyl]-3H-imidazo[4,5-b]pyridine Step 1: Preparation of 2-butyl-3-{2'-[1-(1-ethoxyethyl)-1H-tetrazol-5-yl]-biphenyl-4-ylmethyl}-5-hydroxymethyl-6-(2-phenylethyl-1-yl)-3H-imidazo[4,5-b]pyridine 0.2 g(0.00032 mole) of the compound obtained in step 3 of Example 13 was dissolved in 5 ml of ethanol and to the resulting solution was added 0.02 g of 10% Pd/C. The resultant was stirred for 16 hours under hydrogen(50 psi), passed through Cellite and concentrated under reduced pressure to obtain 0.17 g of the title compound(yield 85%).

Step 2 : Preparation of 2-butyl-5-dimethoxymethyl-6-(2-phenylethyl-1-yl)-3-[2'-(1H-tetrazol-5-yl)-biphenyl-4-ylmethyl]-3H-imidazo[4,5-b]pyridine The same procedure as in step 12 of Example 1 was repeated using 0.15 g(0.00024 mole) of the compound obtained in the above step 1 to obtain 0.12 g of the title compound(yield $^1$H NMR(300 MHz, $CDCl_3$)δ0.73(t, 3H), 1.20(m, 2H), 1.60(m, 2H), 2.56(t, 2H), 2.86(m, 2H), 3.04(m, 2H), 5.24(s, 2H), 5.33(s, 1H), 6.67(d, 2H), 6.80(d, 2H), 7.04~7.30(m, 10 H), 7.60(d, 1H), 7.76(s, 1H).

EXAMPLE 16

Preparation of 2-butyl-5-dimethoxymethyl-6-(4-methylphenyl-1-yl)-3-[2'-(1H-tetrazol-5-yl)-biphenyl-4-ylmethyl]-3H-imidazo[4,5-b]pyridine The same procedures as in the steps 8 to 12 of Example 1 were repeated using 0.54 g(0.00135 mole) of the compound obtained in step 7 of Example 1 and 0.55 g(0.00405 mole) of 4-methylphenylboric acid to obtain 0.122 g of the title compound(yield 19%).

¹H NMR(300 MHz, CDCl₃)δ0.90(t, 3H), 1.40(m, 2H), 1.75(m, 2H), 2.43(s, 3H), 2.78(t, 2H), 3.30(s, 6H), 5.28(s, 1H), 5.50(s, 2H), 6.95(m, 4H), 7.30(m, 4H), 7.43(m, 3H), 7.65(s, 1H), 7.93(d, 1H).

EXAMPLE 17

Preparation of 2-butyl-5-dimethoxymethyl-6-[4-(benzyloxymethyl)-phenyl-1-yl]-3-[2'-(1H-tetrazol-5-yl)-biphenyl-4-ylmethyl]-3H-imidazo[4,5-b]pyridine The same procedures as in the steps 8 to 12 of Example 1 were repeated using 0.001 g(0.00249 mole) of the compound obtained in step 7 of Example 1 and 1.5 g(0.00623 mole) of 4-(benzyloxymethyl)phenylboric acid to obtain 0.25 g of the title compound(yield 15%).

¹H NMR(300 MHz, CD₃OD)δ0.95(t, 3H), 1.4(m, 2H), 1.75(m, 2H), 2.9(t, 2H), 3.35(s, 6H), 4.65(s, 2H), 4.69(s, 2H), 5.3(s, 1H), 5.7(s, 2H), 7.1(d, 2H), 7.18(d, 2H), 7.4(m, 6H), 7.62(m, 2H), 7.85(s, 1H).

EXAMPLE 18

Preparation of 2-butyl-5-dimethoxymethyl-6-(4-hydroxymethylphenyl-1-yl)-3-[2'-(1H-tetrazol-5-yl)-biphenyl-4-ylmethyl]-3H-imidazo[4,5-b]pyridine 0.05 g(0.074 mole) of the compound obtained in Example 17 was dissolved in 3 ml of methanol and to the resulting solution was added 0.005 g of Pd/C. The resultant was reacted for 18 hours under hydrogen(40 psi) using a hydrogenation apparatus and filtered through Cellite to remove palladium. Thereafter the filtrate was evaporated under reduced pressure and purified with column chromatography (10% methanol/dichloro-methane) to obtain 0.035 g of the title compound(yield 80%).

¹H NMR(300 MHz, CD₃OD) δ0.9(t, 3H), 1.4(m, 2H), 1.75(m, 2H), 2.88(t, 2H), 3.3(s, 6H), 4.7(s, 2H), 5.3(s, 1H), 5.54(s, 2H), 7.1(s, 4H), 7.4(m, 7H), 7.62(d, 1H), 7.8(s, 1H).

EXAMPLE 19

Preparation of 2-butyl-5-dimethoxymethyl-6-(2-nitrophenyl-1-yl)-3-[2'-(1H-tetrazol-5-yl)-biphenyl-4-ylmethyl]-3H-imidazo[4,5-b]pyridine Step 1: Preparation of 2-butyl-5-hydroxymethy1-6-(2-nitrophenyl-1-yl)-3H-imidazo[4,5-b]pyridine 1 g(0.00356 mole) of 2-butyl-5-hydroxymethyl-6-phenyl-3H-imidazo[4,5-b]pyridine obtained in step 9 of Example 1 was dissolved in 4 ml of conc. sulfuric acid and to the resulting solution was added 0.32 ml(61%, 0.00427 mole) of nitric acid at 0° C. The reaction solution was stirred for 10 minutes, neutralized with ammonia water and extracted with ethyl acetate(30 ml×2). The residue was dried over Na₂SO₄ and concentrated under reduced pressure. The remaining was purified with column chromatography (ethyl acetate) to obtain 0.6 g of the title compound(yield 52%).

Step 2: Preparation of 2-butyl-5-dimethoxymethyl-6-(2-nitrophenyl-1-yl)-3-[2'-(1H-tetrazol-5-yl)-biphenyl-4-ylmethyl3-3H-imidazo[4,5-b]pyridine The same procedures as in the steps 10 to 12 of Example 1 were repeated using 0.5 g(0.00153 mole) of the compound obtained in the above step 1 to obtain 0.39 g of the title compound(yield 41%).

¹H NMR(300 MHz, CD₃OD)δ0.91(t, 3H), 1.40(m, 2H), 1.72(m, 2H), 2.90(t, 2H), 3.29(s, 6H), 5.27(d, 1H), 5.64(s, 2H), 7.12~8.37(m, 13H).

EXAMPLE 20

Preparation of 2-butyl-5-dimethoxymethyl-6-(2-methoxyphenyl-1-yl)-3-[2'-(1H-tetrazol-5-yl)-biphenyl-4-ylmethyl]-3H-imidazo[4,5-b]pyridine Step 1: Preparation of 2-butyl-5-hydroxymethyl-3-(2-oxo-2-phenylethyl)-6-(2-methoxyphenyl-1-yl)-3H-imidazo[4,5-b]pyridine The same procedure as in step 8 of Example 1 was repeated using 1.2 g(0.003 mole) of the compound obtained in step 7 of Example 1 and 1.37 g(0.009 mole) of 2-methoxyphenylboric acid to obtain 0.86 g of the title compound(yield 67%).

Step 2: Preparation of 2-butyl-5-dimethoxymethyl-6-(2-methoxyphenyl-1-yl)-3-[2'-(1H-tetrazol-5-yl)-biphenyl-4-ylmethyl]-3H-imidazo[4,5-b]pyridine The same procedures as in steps 9 to 12 of Example 1 were repeated using 0.5 g(0.00117 mole) of the compound obtained in the above step 1 to obtain 0.27 g of the title compound(yield 39%).

¹H NMR(300 MHz, CD₃OD)δ0.92(t, 3H), 1.40(m, 2H), 1.72(m, 3H), 2.89(t, 2H), 3.31(s, 6H), 3.87(s, 3H), 5.29(s, 1H), 5.65(s, 2H), 7.03~7.55(m, 12H), 7.81(s, 1H).

EXAMPLE 21

Preparation of 2-butyl-5-dimethoxymethyl-6-(1-oxy-pyridin-2-yl)-3-[2'-(1H-tetrazol-5-yl)-biphenyl-4-ylmethyl]-3H-imidazo[4,5-b]pyridine Step 1: Preparation of 2-butyl-5-dimethoxymethyl-6-(1-oxy-pyridin-2-yl)-3-[2'-[1-(1-ethoxyethyl)-1H-tetrazol-5-yl]-biphenyl-4-ylmethyl]-3H-imidazo[4,5-b]pyridine 0.1 g(0.00016 mole) of the compound obtained in step 4 of Example 8 was dissolved in 2 ml of dichloromethane and to the resulting solution was added 0.033 g(0.00019 mole) of 3-chloroperoxybenzoic acid. The resultant was stirred for 16 hours at room temperature and concentrated under reduced pressure. The residue was purified with column chromatography (5% methanol/dichloromethane) to obtain 0.068 g of the title compound(yield 66%).

Step 2: Preparation of 2-butyl-5-dimethoxymethyl-6-(1-oxy-pyridin-2-yl)-3-[2'-(1H-tetrazol-5-yl)-biphenyl-4-ylmethyl]-3H-imidazo[4,5-b]pyridine 0.068 g(0.00011 mole) of the compound obtained in the above step 1 was dissolved in 3 ml of 3% HCl/MeOH (anhydrous) and stirred for 30 minutes at room temperature. To the resulting solution was added saturated NaHCO₃ solution. The resultant was extracted with ethyl acetate and dried over MgSO₄. The organic phase was concentrated under reduced pressure and purified with column chromatography (40% methanol/dichloromethane) to obtain 0.051 g of the title compound(yield 81%).

¹H NMR(200 MHz, CD₃OD)δ0.85(t, 3H), 1.3(m, 2H), 1.7(m, 2H), 2.85 (t, 2H), 3.3(s, 6H), 5.5(s, 1H), 5.6(s, 2H), 7.05(s, 4H), 7.5(m, 7H), 7.9(s, 1H), 8.35 (d, 1H).

EXAMPLE 22

Preparation of 2-butyl-5-dimethoxymethyl-6-(pyridin-3-yl)-3-[2'-(1H-tetrazol-5-yl)-biphenyl-4-ylmethyl]-3H-imidazo[4,5-b]pyridine 0.4 g(0.00063 mole) of the compound obtained in step 7 of Example 1 was reacted with 3-tributyltin pyridine similarly to step 1 of Example 8. The resultant was reacted as in the procedures of steps 4 and 5 of Example 8 to obtain 0.06 g of the title compound(yield 17%).

'NMR(200 MHz. CDCl$_3$)δ0.92(t, 3H), 7.42(m, 2H), 1.78 (m, 2H), 2.72(t, 2H), 3.30(s, 6H), 5.18(s, 1H), 5.38 (s, 2H), 6.98(d, 4H), 7.28(s, 1H), 7.49(m, 4H), 7.75(d, 1H), 7.90(d, 1H), 8.45(s, 1H), 8.68(d, 1H).

EXAMPLE 23

Preparation of 2-butyl-5-dimethoxymethyl-6-(pyridin-4-yl)-3-[2'-(1H-tetrazol-5-yl)-biphenyl-4-ylmethyl]-3H-imidazo[4,5-b]pyridine The same procedures as in the steps 4 and 5 of Example 8 were repeated using 0.4 g(0.00063 mole) of the compound obtained in step 7 of Example 1 and 4-tributyltin pyridine to obtain 0.18 g of the title compound(yield 51%).

'H NMR(200 MHz, CDCl$_3$) 0.95(t, 3H), 1.42(m, 2H), 1.81(m, 2H), 2.82(t, 3H), 3.38(s, 6H), 5.20(s, 1H), 5.55 (s, 2H), 7.02(s, 4H), 7.26(m, 2H), 7.39 (m, 1H), 7.51(m, 2H), 7.7(s, 1H), 7.92 (d, 1H), 8.39(d, 2H).

EXAMPLE 24

Preparation of 2-butyl-5-dimethoxymethyl-6-(1-oxy-pyridin-3-yl)-3-[2'-(1H-tetrazol-5-yl)-biphenyl-4-ylmethyl]-3H-imidazo[4,5-b]pyridine The same procedure as in Example 21 was repeated using 0.1 g(0.00015 mole) of the compound obtained in Example 22 to obtain 0.078 g of the title compound(yield 85%).

'H NMR(200 MHz, CD$_3$OD)δ0.85(t, 3H), 1.3(m, 2H), 1.65(m, 2H), 2.85(m, 2H), 3.3(s, 6H), 5.3(s, 1H), 5.6(s, 2H), 7.05(d, 4H), 7.5(m, 5H), 7.9(m, 2H), 8.3(d, 1H), 8.45(s, 1H).

EXAMPLE 25

Preparation of 2-butyl-5-dimethoxymethyl-6-(1-oxy-pyridin-4-yl)-3-[2'-(1H-tetrazol-5-yl)-biphenyl-4-ylmethyl)-3H-imidazo[4,5-b]pyridine The same procedure as in Example 21 was repeated using 0.05 g(0.00008 mole) of the compound obtained in Example 23 to obtain 0.028 g of the title compound(yield 61%).

'H NMR(200 MHz, CDCl$_3$+CD$_3$OD) 0.9(t, 3H), 1.4(m, 2H), 1.75(m, 2H), 2.8(t, 2H), 3.35(s, 6H), 5.3(s, 1H), 5.52(s, 2H), 7.08(s, 4H), 7.5(m, 6H), 7.85(s, 1H), 8.3(d, 2H).

EXAMPLE 26

Preparation of 2-butyl-5-dimethoxymethyl-6-(2-aminophenyl-1-yl)-3-[2'-(1H-tetrazol-5-biphenyl-4-ylmethyl]-3H-imidazo[4,5-b]pyridine Step 1: Preparation of 2-butyl-5-methyl-6-phenyl-1H-imidazo[4,5-b]pyridine The same procedure as in step 8 of Example 1 was repeated using 6.0 g(0.0224 mole) of 6-bromo-2-butyl-5-methyl-1H-imidazo[4,5-b]pyridine obtained in step 4 of Example 1 to obtain 5.64 g of the title compound(yield 95%).

Step 2: Preparation of 2-butyl-5-methyl-6-(2-nitrophenyl-1-yl)-1H-imidazo[4,5-b]pyridine 3.0 g(0.01132 mole) of the compound obtained in the above step 1 was dissolved in 20 ml of sulfuric acid and cooled to 0° C. in an ice bath. To the resulting solution was added 0.79 ml(0.01358 mole) of nitric acid dropwise with stirring. The resultant was reacted for 30 minutes and was added into 150 ml of ice water slowly to terminate the reaction. The reactant was neutralized with 6N sodium hydroxide and extracted with ethyl acetate(100 ml×2). The organic layer was dried over anhydrous sodium sulfate, concentrated under reduced pressure and recrystallized from hexane:ethyl acetate (1:3) to obtain 1.5 g of the title compound(yield 43%).

Step 3: Preparation of 2-butyl-5-hydroxymethyl-6-(2-nitrophenyl-1-yl)-1H-imidazo[4,5-b]pyridine The same procedures as in steps 5 and 6 of Example 1 were repeated using 1.5 g(0.00483 mole) of the compound obtained in the above step 2 to obtain 0.72 g of the title compound.

Step 4: Preparation of 2-butyl-5-dimethoxymethyl-6-(2-nitrophenyl-1-yl)-1H-imidazo[4,5-b]pyridine The same procedures as in steps 11 and 12 of Example 1 were repeated using 0.7 g(0.00214 mole) of the compound obtained in the above step 3 to obtain 0.38 g of the title compound.

Step 5: Preparation of 2-butyl-3-{2'-[1-(1-ethoxyethyl)-1H-tetrazol-5-yl]-biphenyl-4-ylmethyl}-5-dimethoxymethyl-6-(2-nitrophenyl-1-yl)-1H-imidazo[4,5-b]pyridine The same procedure as in step 10 of Example 1 was repeated using 0.32 g(0.00086 mole) of the compound obtained in the above step 4 to obtain 0.43 g of the title compound(yield 75%).

Step 6: Preparation of 2-butyl-3-{2'-[1-(1-ethoxyethyl)-1H-tetrazol-5-yl)-biphenyl-4-ylmethyl}-5-dimethoxymethyl-6-(2-aminophenyl-1-yl)-1H-imidazo[4,5-b]pyridine The same procedure as in step 2 of Example 11 was repeated using 0.2 g(0.00029 mole) of the compound obtained in step 5 to obtain 0.17 g of the title compound (yield 91%).

Step 7: Preparation of 2-butyl-5-dimethoxymethyl-6-(2-aminophenyl-1-yl)-3-[2'-(1H-tetrazol-5-yl)-biphenyl-4-ylmethyl]-3H-imidazo[4,5-b]pyridine 0.15 g(0.00023 mole) of the compound obtained in the above step 6 was dissolved in 5 ml of methanol and to the resulting solution was added 1 ml of 3% anhydrous HCl/MeOH. The resultant was refluxed for 1 hour and purified by the same procedure as in step 12 of Example 1 to obtain 0.12 g of the title compound in a white solid form(yield 92%).

'NMR(200 MHz. CDCl$_3$)δ0.87(t, 3H), 1,35(m, 2H), 1.70 (m, 2H), 2.70(t, 2H), 3.30(s, 6H), 5.35(s, 1H), 5.50(s, 2H), 6.55~7.57(m, 12H), 7.8(m, 1H).

EXAMPLE 27

Preparation of 2-butyl-5-dimethoxymethyl-6-benzyl-3-[2'-(1H-tetrazol-5-yl)-biphenyl-4-ylmethyl]-3H-imidazo[4,5-b]pyridine Step 1: Preparation of 2-butyl-5-methyl-6-styryl-1H-imidazo[4,5-b]pyridine The same procedure as in step 8 of Example 1 was repeated using 4.0 g(0.0133 mole) of the compound obtained in step 4 of Example 1 and 3.0 g(0.0203 mole) of styrylboric acid to obtain 4.0 g of the title compound(yield 93%).

Step 2: Preparation of 2-butyl-5-methyl-6-formyl-1H-imidazo[4,5-b]pyridine 4.0 g(0.0124 mole) of the compound obtained in the above step 1 was dissolved in a mixture of 60 ml of dioxane and 20 ml of distilled water and to the resulting solution was added 0.25 ml(0.00012 mole) of osmium tetraoxide and 6.63 g(0.0166 mole) of sodium periodate. The resultant was stirred for 20 hours at room temperature and concentrated under reduced pressure. The residue was diluted with 250 ml of methylene chloride and washed with water(250 ml×2). The organic layer was dried over Na$_2$SO$_4$ and the residue was concentrated under reduced pressure and purified with column chromatography (ethyl acetate) to obtain 2.16 g of the title compound(yield 70%).

Step 3: Preparation of 2-butyl-5-methyl-6-formyl-3-(toluene-4-sulfonyl)-1H-imidazo[4,5-b]pyridine 2.0 g(0.00803 mole) of the compound obtained in the above step 2 was dissolved in 20 ml of dimethylene chloride and to the resulting solution were added 1.7 ml(0.012 mole) of triethylamine and 1.84 g(0.00964 mole) of 4-toluene sulfonylchloride. The resultant was stirred for 16 hours at room temperature and concentrated under reduced pressure. The residue was purified with column chromatography (hexane:ethyl acetate =2:1) to obtain 2.73 g of the title compound(yield 84%).

Step 4: Preparation of 2-butyl-5-methyl-6-[(hydroxy)(phenyl)-methyl]-3-(toluene-4-sulfonyl)-1H-imidazo[4,5-b]pyridine 2.5 g(0.00619 mole) of the compound obtained in the above step 3 was dissolved in 15 ml of tetrahydrofuran and stirred for 10 minutes at 0° C. while adding 6.2 ml(0.0062 mole of 3M phenyl magnesium bromide. 100 ml of water was added to the resulting solution and, thereafter, the reaction solution was diluted with 100 ml of ethyl acetate. The organic layer was dried over anhydrous $Na_2SO_4$ and concentrated under reduced pressure. The residue was purified with column chromatography (hexane:ethyl acetate =1:1) to obtain 2.76 g of the title compound(yield 99%).

Step 5: Preparation of 2-butyl-5-methyl-6-[(chloro)(phenyl)-methyl]-3-(toluene-4-sulfonyl)-1H-imidazo(4,5-b]pyridine The same procedure as in the above step 3 was repeated using 2.0 g(0.00444 mole) of the compound obtained in the above step 4, 0.7 ml(0.00888 mole) of methanesulfonylchloride and 1.92 ml(0.0133 mole) of triethylamine to obtain 1.91 g of the title compound(yield 92%).

Step 6: Preparation of 2-butyl-5-methyl-6-benzyl-3-(toluene-4-sulfonyl)-1H-imidazo[4,5-b]pyridine 1.5 g(0.0032 mole) of the compound obtained in the above step 5 was dissolved in 20 ml of toluene and to the resulting solution was added 1.8 ml(0.0064 mole) of tributyltin hydride and 0.087 g(0.00064 mole) of AIBN. The resultant was refluxed for 30 minutes and concentrated under reduced pressure. The residue was purified with column chromatography (hexane → hexane:ethyl acetate =1:1) to obtain 1.15 g of the title compound(yield 83%).

Step 7: Preparation of 2-butyl-5-methyl-6-benzyl-1H-imidazo-[4,5-b]pyridine 1.0 g(0.0023 mole) of the compound obtained in the above step 6 was dissolved in 10 ml of methanol and to the resulting solution was added 6.4 ml(0.0064 mole) of aqueous 1N sodium hydroxide solution. The resultant was stirred for 30 minutes at room temperature and concentrated under reduced pressure. The residue was neutralized aqueous 1N HCl solution and diluted with 50 ml of ethyl acetate. The organic layer was dried over anhydrous $Na_2SO_4$ and concentrated under reduced pressure. The residue was purified with column chromatography (ethyl acetate → 10% MeOH/$CH_2Cl_2$) to obtain 0.51 g of the title compound(yield 80%).

Step 8: Preparation of 2-butyl-5-methyl-6-benzyl-1H-imidazo[4,5-b]pyridine-4-oxide The same procedure as in step 5 of Example 1 was repeated using 0.5 g(0.00179 mole) of the compound obtained in the above step 7 to obtain 0.53 g of the title compound(yield 100%).

Step 9: Preparation of 2-butyl-5-hydroxymethyl-6-benzyl-1H-imidazo[4,5-b]pyridine The same procedure as in step 6 of Example 1 was repeated using 0.53 g(0.00179 mole) of the compound obtained in the above step 8 to obtain 0.42 g of the title compound(yield 80%).

Step 10: Preparation of 2-butyl-5-formyl-6-benzyl-1H-imidazo-[4,5-b]pyridine

The same procedure as in step 11 of Example 1 was repeated using 0.42 g(0.00142 mole) of the compound obtained in the above step 9 to obtain 0.31 g of the title compound(yield 75%).

Step 11: Preparation of 2-butyl-5-formyl-6-benzyl-3-{2'-[1-(1-ethoxyethyl)-1H-tetrazol-5-yl]-biphenyl-4-ylmethyl}-3H-imidazo(4,5-b]pyridine The same procedure as in step 10 of Example 1 was repeated using 0.31 g(0.00106 mole) of the compound obtained in the above step 10 to obtain 0.38 g of the title compound(yield 60%).

Step 12: Preparation of 2-butyl-5-dimethoxymethyl-6-benzyl-3-[2'-(1H-tetrazol-5-yl)-biphenyl-4-ylmethyl]-3H-imidazo[4,5-b]pyridine The same procedure as in step 12 of Example 1 was repeated using 0.38 g(0.00063 mole) of the compound obtained in the above step 11 to obtain 0.36 g of the title compound(yield 100%)

'NMR(200 MHz, DMSO-$d_3$)δ0.90(t, 3H), 1.35(m, 2H), 1.70(m, 2H), 2.88(m, 2H), 4.35(s, 2H), 5.53(d, 3H), 7.15(m, 4H), 728(m, 5H), 7.63(m, 5H)

EXAMPLE 28

Preparation of 2-butyl-5-dimethoxymethyl-6-phenyl-7-methyl-3-[2'-(1H-tetrazol-5-yl)-biphenyl-4-ylmethyl]-3H-imidazo[4,5-b]pyridine Step 1: Preparation of 2-amino-4,6-dimethyl-5-bromopyridine 20 g(0.164 mole) of 2-amino-4, 6-dimethylpyridine was added into a mixture of 69 ml of water and 16.1 g(0.164 mole) of sulfuric acid and the resulting solution was cooled to 0° C., and thereto was added 8.45 ml(0.164 mole) of bromine gradually at 0° C. The resulting solution was stirred for 30 minutes, adjusted to pH 9 to 10 with aqueous sodium hydroxide solution and extracted with dichloromethane. The organic layer was washed with water, dried over anhydrous $Na_2SO_4$ and concentrated under reduced pressure. The residue was purified with silica gel column chromatography to obtain 18.25 g of the title compound(yield 55%) and 5.4 g of dibromo compound(yield 11.8%).

Step 2: Preparation of 2-amino-3-nitro-4,6-dimethyl-5-bromo-pyridine 51 ml of sulfuric acid was cooled to 0° C. and thereto was added 16.85 g(0.08383 mole) of the compound obtained in the above step 1 gradually at 0° C. To the resulting solution 9 g(0.0857 mole) of 60% nitric acid was added gradually at 0° C. The resultant was stirred for 1 hour at 0° C. and subsequently, stirred for another 1 hour at room temperature, and was added to ice and adjusted to pH about 6 with aqueous sodium hydroxide solution at 0° C. The resultant was filtered and washed with water, then dried in air.

Step 3: Preparation of 2,3-diamino-4,6-dimethyl-5-bromo-pyridine 70 ml of ethanol, 10 ml of distilled water, 0.75 ml of conc. HCl and 46.35 g(0.83 mole) of iron powder were added to the compound obtained in the above step 2 and the resultant was refluxed for 30 minutes, filtered through Cellite, and washed with hot ethanol, then concentrated under reduced pressure. The residue was purified with silica gel column chromatography to obtain 15.08 g of the title compound (yield 82%).

Step 4: Preparation of 6-bromo-2-butyl-5,7-dimethyl-1H-imidazo[4,5-b]pyridine 10 ml(0.1 mole) of valeric acid and 130 g of polyphosphoric acid were added to 14.72 g(0.068148 mole) of the compound obtained in the above step 3 and the reaction solution was stirred for about 1 hour at 110° C., and then added to ice and adjusted to pH about 8 with aqueous sodium hydroxide solution. The resultant was extracted with 400 ml of ethyl acetate and, thereafter the organic layer was washed with 200 ml of aqueous sodium bicarbonate solution, dried over anhydrous sodium sulfate and concentrated under reduced pressure. The residue was recrystallized from ethyl acetate-hexane to obtain 16.26 g of the title compound(yield 84.6%).

Step 5: Preparation of 2-butyl-5,7-dimethyl-6-phenyl-1H-imidazo[4,5-b]pyridine 5.14 g(0.01823 mole) of the compound obtained in the above step 4 was dissolved in a mixture of 100 ml of dimethoxyethane and 20 ml of distilled water and thereto were added 4.4 g(0.03609 mole) of phenylboric acid, 0.72 g(0.0006:23 mole) of Pd(PPh$_3$)$_4$ and 19 g of K$_3$PO$_4$.nH$_2$O. The resultant was refluxed for 16 hours and extracted with 200 ml of ethyl acetate. The organic layer was dried over anhydrous sodium sulfate, concentrated under reduced pressure and purified with silica gel column chromatography to obtain 4.23 g of the title compound(yield 83%).

Step 6: Preparation of 2-butyl-5,7-dimethyl-6-phenyl-1H-imidazo[4,5-b]pyridine-4-oxide 3.23 g(0.01158 mole) of the compound obtained in the above step 5 was dissolved in 50 ml of methylene chloride and to the resulting solution was added 4.79 g(0.01389 mole) of 50% 3-chloroperoxybenzoic acid. The resultant was stirred for 30 minutes at room temperature and concentrated under reduced pressure. The residue was purified with silica gel column chromatography to obtain 2.84 g of the title compound(yield 83%).

Step 7: Preparation of 2-butyl-5-hydroxymethyl-6-phenyl-7-methyl-1H-imidazo[4,5-b]pyridine 10 ml of anhydrous acetic acid was added to 2.52 g(0.00854 mole) of the compound obtained in the above step 6 and the resulting solution was stirred for 1.5 hours at 120° C., concentrated under reduced pressure and thereto were added 13 ml of 4N aqueous sodium hydroxide solution and 20 ml of methanol. The reactant was refluxed for about 30 minutes and neutralized with 4N aqueous hydrochloric solution. The resultant was adjusted to be weak alkaline with aqueous sodium bicarbonate solution and extracted with ethyl acetate. The organic layer was dried over anhydrous sodium sulfate. The residue was concentrated under reduced pressure to obtain 2.19 g of a mixture of the title compound and 2-butyl-5-methyl-6-phenyl-7-hydroxymethyl-1H-imidazo[4,5-b]pyridine.

Step 8: Preparation of 2-butyl-5-hydroxymethyl-6-phenyl-7-methyl-3-{2'-[1-(1-ethoxyethyl)-1H-tetrazol-5-yl]-biphenyl-4-ylmethyl}-3H-imidazo[4,5-b]pyridine 12 ml of dimethylformamide and 3.54 g(0.02562 mole) of potassium carbonate were added to 2.19 g of the mixture obtained in the above step 7 and to the resulting solution was added 2.34 g(0.006 mole) of 2'-[1-(1-ethoxyethyl)-1H-tetrazol-5-yl]-biphenyl-4-ylmethylbromide. The resultant was stirred for 1.5 hours at room temperature and extracted with 100 ml of ethyl acetate and 50 ml of water. The organic layer was dried over anhydrous sodium sulfate. The residue was concentrated under reduced pressure and purified with silica gel column chromatography to obtain 0.698 g of the title compound(yield 18%).

Step 9: Preparation of 2-butyl-5-formyl-6-phenyl-7-methyl-3-{2'-[1-(1-ethoxyethyl)-1H-tetrazol-5-yl]-biphenyl-4-ylmethyl}-3H-imidazo[4,5-b]pyridine 0.1849 g(0.000308 mole) of the compound obtained in the above step 8 was dissolved in 5 ml of methylene chloride and to the resulting solution was added 0.57 g(0.00656 mole) of manganese dioxide. The resultant was stirred for 16 hours at room temperature and filtered through Cellite. The filtrate was concentrated under reduced pressure and purified with silica gel column chromatography to obtain 0.1376 g of the title compound(yield 74.6%).

Step 10: Preparation of 2-butyl-5-dimethoxymethyl-6-phenyl-7-methyl-3-[2'-(1H-tetrazol-5-yl)-biphenyl-4-ylmethyl]-3H-imidazo[4,5-b]pyridine 0.181 g(0.000302 mole) of the compound obtained in the above step 9 was dissolved in 1 ml of methanol and to the resultant solution was added 2 ml of 3% hydrogen chloride-methanol solution. The resultant was refluxed for 2 hours and to the reactant was added sodium carbonate. The resulting solution was stirred for about 5 minutes, filtered and concentrated under reduced pressure. The residue was purified with silica gel column chromatography to obtain 0.160 g of the title compound(yield 92%).

$^1$H NMR(CD$_3$OD) δ0.87(t, 3H), 1.32(m, 2H), 1.62(m, 2H), 2.29(s, 3H), 2.82(t, 2H), 3.18(s, 6H), 4.97(s, 1H), 5.62(s, 2H), 7.08(q, 4H), 7.22(m, 2H), 7.3~7.60(m, 7H).

EXAMPLE 29

Preparation of 2-butyl-5-methyl-6-phenyl-7-dimethoxymethyl-3-[2'-(1H-tetrazol-5-yl)-biphenyl-4-ylmethyl]-3H-imidazo 4, 5-b]pyridine Step 1: Preparation of 2-butyl-5-methyl-6-phenyl-7-hydroxymethyl-3-{2'-[1-(1-ethoxyethyl)-1H-tetrazol-5-yl]-biphenyl-4-ylmethyl}-3H-imidazo[4,5-b]pyridine The same procedures as in steps 1 to 8 of Example 28 were repeated and thereafter, the resultant was purified with silica gel column chromatography to obtain 1.40 g of the title compound which is a diastereomer of the compound obtained in step 8 of Example 28(yield 37%).

$^1$H NMR(200 MHz, CDCl$_3$)δ0.90(t, 3H), 1.08(t, 3H), 1.40(m, 2H), 1.65(d, 3H), 1.75(m, 2H), 2.35 (s, 3H), 2.75(t, 2H), 3.20–3.50(m, 2H), 4.80(s, 2H), 5.50(s, 2H), 5.88(q, 1H), 7.15(m, 6H), 7.45(m, 6H), 7.85(dd, 1H).

Step 2: Preparation of 2-butyl-5-methyl-6-phenyl-7-formyl-3-{2'[1-(1-ethoxyethyl)-1H-tetrazol-5-yl]-biphenyl-4-ylmethyl}-3H-imidazo[4,5-b]pyridine 1.40 g(0.0023 mole) of the compound obtained in the above step 1 was dissolved in a mixture of 7 ml of methylene chloride and 7 ml of dimethylsulfoxide and to the resulting solution were added 1.92 ml(0.0138 mole) of triethylamine and subsequently 1.46 g(0.0092 mole) of sulfur trioxide pyridine (SO$_3$Py) gradually. The resultant was stirred for 6 hours at room temperature and to the resulting solution was added 20 ml of water to terminate the reaction. The resulting solution was extracted with ethyl acetate(30 ml×2). The organic layer was washed with 30 ml of saturated sodium chloride solution, dried over anhydrous magnesium sulfate, filtered and concentrated under reduced pressure to obtain 1.34 g of the title compound(yield 96%).

$^1$H NMR(200 MHz, CDCl$_3$)δ0.90(t, 3H), 1.08(t, 3H), 1.40(m, 2H), 1.65(d, 3H), 1.75(m, 2H), 2.42(s, 3H), 2.85(t, 2H), 3.20–3.50(m, 2H), 5.52(s, 2H), 5.90(q, 1H), 7.10(n, 4H), 7.30–7.55(m, 8H), 7.88(dd, 1H), 10.10(s, 1H).

Step 3: Preparation of 2-butyl-5-methyl-6-phenyl-7-dimethoxymethyl-3-[2'-(1H-tetrazol-5-yl)-biphenyl-4-ylmethyl]-3H-imidazo[4, 5-b]pyridine 1.34 g(0.0022 mole) of the compound obtained in the above step 2 was reacted as in the same procedure of step 10 of Example 28 to obtain 1.11 g of the title compound(yield 88%).

$^1$H NMR(200 MHz, CDCl$_3$)δ0.85(t, 3H), 1.33(m, 2H), 1.55(m, 2H), 2.30(s, 3H), 2.90(t, 2H), 5.05(s, 1H), 5.60(s, 2H), 7.08(m, 4H), 7.20(m, 2H), 7.40–7.60 (m, 7H).

Activity Test

The inventive compounds were tested to measure their angiotensin II receptor binding capacity, lowering effect of blood pressure in renal hypertension and sustainability as follows. Losartan(Dup 753) and 5,7-dimethyl-2-ethyl-3-[2'-tetrazol-5-yl)-biphen-4-yl]methyl-3H-imidazo [4,5-b] pyridine(referred to as the "Merck compound" throughout this specification), which is disclosed in EP No. 400,974 issued to Merck, were used as the control compounds.

1. Angiotensin II Receptor Binding Assay

In accordance with the procedure disclosed in Chiu, A. T. et al., *Eur. J. Pharm.*, 157, 13(1981), a ligand marked with a radioisotope was reacted with an angiotensin II receptor and the reactant was filtered with a glass fiber to remove unreacted ligand. After washing the filter, the amount of the remaining isotope was measured to determine the binding activity of the ligand, as described below in detail.

(i) Isolation of Angiotensin II Receptor

Sprague-Dawley rats and Wistar rats of 250 to 350 g(from The Korea Research Institute of Chemical Technology) were tested and the test procedures were carried out at 4° C., unless otherwise specified. Adrenal gland was separated from the Sprague-Dawley rats(liver, in the case of Wistar rats) into cortex and medulla. The separated adrenal cortex and medulla were washed with a sucrose buffer solution (0.2M sucrose, 1 mM EDTA, 10 mM Tris, pH 7.2) and homogenized in the same buffer solution by using a Teflon pestle and a Brinkmann homogenizer. The homogenates were centrifuged at 3,000 Xg for 10 minutes to remove precipitates and further centrifuged at 12,000 Xg for 13 minutes. The final supernatants were centrifuged at 102,000 Xg for 1 hour to obtain precipitates, which were washed with a Tris buffer solution(50 mM Tris, 5 mM $MgCl_2$, pH 7.2) and re-centrifuged at 102,000 Xg for 1 hour. The resulting precipitates were immediately processed at the following step or stored at −70° C.

The precipitates were suspended in a Tris buffer solution. The amount of protein was determined by using a Bio-Rad DC protein analyzing kit and the protein concentration was adjusted to the amounts of: 0.2 to 0.3 mg/ml(Sprague-Dawley rat: adrenal cortex), 1.5 to 2.0 mg/ml(Sprague-Dawley rat: adrenal medulla), and 1.5 to 2.0 mg/ml(Wistar rat: liver). To the suspension, bovine serum albumin(BSA) was added to a concentration of 0.25 wt % and the resultant was immediately processed at the following step or stored at −70° C.

(ii) Measurement of angiotensin II receptor binding capacity 50 μl(based on ligand) of [$^3$H] angiotensin II(NEN, NET-446) and 10 μl of each of the test compounds with various concentrations were added to the buffer solution(50 mM Irris(pH 7.2), 5 mM $MgCl_2$, 0.25% BSA) to adjust the final volume to be 0.5 ml. 100 μl of the receptor suspension was added thereto and the resulting solution was reacted for 60 minutes while stirring in a water bath at 25° C. 3 ml of cold buffer solution for analysis was added to cease the reaction. The isotope which was bound to the receptor was isolated from the resultant by using Brandel Cell Harvester System with Whatman glass fiber GF/C. After washing the filter, the radioactivity of the filter was determined by using a liquid scintillation counter. Binding inhibition(%) of the test compound was calculated as follows:

Binding Inhibition(%)=[{(T—B)−(S—B)}/(T—B)]×100 wherein T is cpm of the reaction product untreated with the test compound, S is cpm of the reaction product treated with the test compound, and B is cpm of blank test.

The results are given in Table 1.

2. Blood pressure lowering effect in renal hypertension (i) Induction of renal hypertension To induce renal hypertension, left renal artery of 4 week-old male Sprague-Dawley rats(from The Korea Research Institute of Chemical Technology) was ligated. The rats were anesthetized with ether and the surgical region on the left abdomen of the rat was shaved, disinfected, and then incised about 1 cm vertically. The renal artery near abdominal aorta was isolated carefully from surrounding tissues and veins, and then ligated completely with a suture(4/0 sterile surgical silk). The muscular strata and skin of the surgical area were sutured with a suture(4/0 sterile surgical silk). The surgical region was disinfected to prevent infection and thereafter, 200 to 250 mg/Kg/day of cephazolin sodium was injected intramuscularly for 2 days. 6 to 8 days after the ligation, rats showing systolic pressure of more than 180 mmHg were selected for renal hypertension test. The blood pressure was determined by a tail-cuff method from the tail under unanesthetized condition(Gerold, M. et al., *Arzneimittrel-Forsch*, 18, 1285(1968)).

(ii) Blood pressure lowering effect of the compounds

Each of the compounds to be tested was administered intravenously or orally into the renal hypertensive rat. The blood pressure of the rats was determined by direct method (Chiu, A. T. et al., *J. Pharmacol. Exp. Ther.* 250, 867(1989)) using a catheter. The rats were anesthetized with ketamine hydrochloride(125 mg/kg, i.p.) and a catheter was filled with saline and inserted into a carotid artery and carotid vein. The surgical area was sutured with a metal clip. The rats were relaxed at least 3 hours and the catheter in the carotid artery was adapted to an isotec pressure transducer to determine their blood pressure and heart rate with a physiograph (Linearcorder WR3310). After the blood pressure was stabilized, the test compound was administered intravenously or orally. For intravenous administration, the administered volume and washing volume were 1.0 ml/Kg and 0.2 ml, respectively. The blood pressure and heart rate were measured in regular intervals up to 24 hours after the administration of the test compound and compared with those measured after the administration of the control compound Losartan.

The test compound was dissolved in 0.05N KOH for intravenous administration and suspended in Tween 80 for oral administration. The results are given in Table 1.

TABLE 1

| Compound | Binding Inhibition(%) | Maxium Blood Pressure Lowering Effect(%) (Amount) |
|---|---|---|
| Ex.1 | 77.8 | −40%(3 mg) |
| Ex.2 |  | −45%(3 mg) |
| Ex.3 | 70.6 | −27%(3 mg) |
| Ex.4 | 60.9 | −33%(3 mg) |
| Ex.5 | 54.1 |  |
| Ex.6 | 49.0 | −25%(3 mg) |
| Ex.7 | 78.1 |  |
| Ex.8 | 93.4 | −50%(3 mg) |
| Ex.9 | 45.2 |  |
| Ex.10 | 83.6 |  |
| Ex.11 | 52.5 |  |
| Ex.12 | 44.5 |  |
| Ex.13 | 95.0 | −32%(3 mg) |
| Ex.14 | 72.0 |  |
| Ex.15 | 82.0 | −36%(3 mg) |
| Ex.16 | 68.5 |  |
| Ex.17 | 82.0 |  |

TABLE 1-continued

| Compound | Binding Inhibition(%) | Maxium Blood Pressure Lowering Effect(%) (Amount) |
|---|---|---|
| Ex.18 | 89.4 | −33%(3 mg) |
| Ex.19 | 70.9 | −29%(3 mg) |
| Ex.20 | 81.9 | −25%(3 mg) |
| Ex.21 | 92.2 | −20%(3 mg) |
| Ex.22 | 94.8 | −38%(3 mg) |
| Ex.23 | 92.9 | −33%(3 mg) |
| Ex.24 | 94.9 | −18%(3 mg) |
| Ex.25 | 97.0 | −29%(3 mg) |
| Ex.26 | 89.2 | |
| Ex.27 | 87.8 | |
| Ex.28 | 50.5 | −47%(1 mg) |
| Control Compound (Dup 753) | 48.0 | −30%(3 mg) |

As shown in Table 1, the compounds prepared in Examples 1 to 28 have superior or at least equal effects in a low concentration of 1 to 3 mg, compared with those of the control compound in 3 mg.

(iii) Blood pressure lowering effect The present compounds, Losartan(Dup 753) and the Merck compound were administrated orally to rats in 10, 3, 1, 0.3 and 0.1 mg/kg under the same condition as in (ii) and the blood pressure lowering effect was determined. The results are given in Table 2.

TABLE 2

| | (%) Amount (mg/kg) | | | | |
|---|---|---|---|---|---|
| Compound | 10 | 3 | 1 | 0.3 | 0.1 |
| Losartan(Dup 753) | 46 | 30 | | | |
| Merck | | 40 | | | |
| Example 1 | | 38 | 25 | | |
| Example 8 | | 35–37 | 32 | | |
| Example 28 | | | 47 | 13 | |

As shown in Table 2, the present compounds tested above have blood pressure lowering effects superior to that of Losartan(Dup 753) and at least equal to that of the Merck compound, especially the compound of Example 28 has a far superior effect to that of the Merck compound.

3. Blood pressure lowering effect in unanesthetized dogs (i) Blood pressure variation with time A number of dogs were fed freely in a feeding room and those weighing 7 to 12 kg in good health were selected regardless of their gender.

The test dogs were anesthetized with 30 mg/kg of pentobarbital sodium by intravenous injection and the left femoral artery and femoral vein were separated carefully. Silicone catheter, specially prepared and filled with saline treated with heparin(1,000 IU/ml), was cannulated into the blood vessels. After the surgery, the dogs were constrained to measure their blood pressure continuously with Gould 2000 physiograph adapted to a Grass $P_{23}XL$ pressure transducer; and their heart rates were monitored with ECG/Biotacho amplifier. The dogs were tested at least 2 days after the surgery.

10 mg/kg of furosemide was injected intramuscularly 18 hours(in case of intravenous injection, 2 hours) before the beginning of the test (administration of the test compound) to improve the activity of renin in blood plasma. After the injection of furosemide, neither food nor water was provided. The test compound was suspended in Tween 80 and administered in an amount of 20 mg/kg orally. The blood pressure and heart rate were measured up to 8 hours after the administration of each test compound. The results are given in Table 3.

TABLE 3

| | (%) Time (hr) | | | | | |
|---|---|---|---|---|---|---|
| Compound | 0.5 | 1 | 2 | 4 | 6 | 8 |
| Ex. 1 (3 mg) | −31.3 | −32.6 | −34.0 | −33.0 | −30.1 | −25.9 |
| Ex. 8 (1.0 mg) | −32.7 | −29.9 | −33.0 | −26.8 | −25.0 | −19.7 |
| Ex. 28 (1.0 mg) | −3.3 | −18.9 | −27.7 | −33.3 | −29.5 | −27.1 |
| Control (Dup 753) (3 mg) | −11.0 | −12.3 | −12.8 | −9.9 | −10.1 | −8.2 |

As shown in Table 3, the maximum blood pressure lowering effect of the present compounds lasted up to 8 hours after the administration, while that of the control compound lasted up to 2 hours and decreased thereafter.

(ii) Maximum blood pressure lowering effect in a dog

The maximum blood pressure lowering effect of the present compounds and the control compounds were determined in different amounts of administration using the same method as (i) and the results are given in Table 4.

TABLE 4

| | Amount (mg/kg) | | | | |
|---|---|---|---|---|---|
| Compound | 10 | 3 | 1 | 0.3 | 0.1 |
| Losartan(Dup 753) | 23 | 13 | | | |
| Merck | | | | 24 | 20 |
| Example 1 | 41 | 35 | 15 | | |
| Example 8 | | | | 34 | 32 | 17 |
| Example 28 | | | | 33 | 18 | 9 |

4. Duration of action (i) Duration of action in renal hypertensive rats

The present(Example 28) and control(Merck) compounds were tested using the hypertensive rats of test 2(i). 1 mg or 3 mg/kg of each compound was administered orally and blood pressure lowering effect with time was determined to measure the duration of action of the compounds. The results are given in Table 5.

TABLE 5

| | (%) | |
|---|---|---|
| Time (min.) | Example 28(1 mg/kg) | Merck Compound (3 mg/kg) |
| 0 | 0 | 0 |
| 10 | −16 | −15 |
| 20 | −17 | −27 |
| 30 | −18 | −28 |
| 60 | −21 | −26 |
| 90 | −34 | −28 |
| 120 | −33 | −25 |
| 240 | −46 | −40 |
| 360 | −47 | −36 |
| 1320 | −25 | −35 |
| 1440 | −28 | −40 |

As shown in Table 5, the blood pressure lowered by the compound of Example 28 showed −47% at 360 minutes after the administration 1 mg/kg, while that of the Merck compound showed −40% minutes after the administration of 3 mg/kg, which proves that the present compound has a far longer duration of action than the Merck compound.

(ii) Duration of action in furosemide-administered dogs

The compound of Example 8 and the Merck compound were administered orally to the furosemide-administrated dogs as in test 3(i), and blood pressure lowering effect was measured with time. The results are given in Table 6.

TABLE 6

| Time(min.) | (%) Example 8 (1 mg, per os) | Merck Compound (0.33 mg, per os) |
|---|---|---|
| 0 | 0 | 0.0 |
| 10 | 0 | −5.0 |
| 20 | −8 | −12.2 |
| 30 | −16.2 | −14.4 |
| 60 | −23.8 | −20.1 |
| 90 | −26.0 | −24.4 |
| 120 | −30.0 | −19.1 |
| 150 | −31.7 | −24.2 |
| 180 | −31.7 | −18.9 |
| 210 | −31.2 | −17.0 |
| 240 | −32.7 | −17.0 |
| 270 | −33.9 | −13.4 |
| 300 | −34.9 | −14.9 |
| 330 | −37.0 | −15.6 |
| 360 | −35.5 | −15.6 |
| 390 | −36.4 | −11.4 |
| 420 | −34.9 | −10.7 |
| 450 | −33.0 | −11.4 |
| 480 | −33.0 | −13.8 |

As shown in Table 6, the maximum blood pressure lowering effect of the compound of Example 8 lasted up to 8 hours after the administration thereof, while that of the Merck compound lasted up to 2 to 3 hours and decreased thereafter.

5. Metabolite analysis

Enzyme digestion test was executed in order to detect the metabolite of the test compound in vivo.

A liver microsome and NADPH system of male rats were added to each of the present compound(Example 8) and the control compound(Merck), and the mixture was incubated for 1 hour at 37° C. The resultant was extracted with methanol or dichloromethane, and, thereafter, the organic layer was evaporated to obtain a residue. The residue was analyzed using high pressure liquid chromatography.

FIG. 1 is a HPLC chart showing the result of the enzyme digestion test of the Merck compound and the compound of Example B.

As shown in FIG. 1A, the Merck compound has a metabolite, which corresponds to a peak at 10 minutes of retention time, resulting from an enzymatic digestion. In contrast, as shown in FIG. 1B, the compound of Example 8 has no metabolite from the enzymatic digestion. Such result proves that the present compound has a good stability against the enzymatic digestion, in contrast with the Merck compound.

While the invention has been described in connection with the specific embodiments contained herein, it should be recognized that various modifications and changes may be made and also fall within the scope of the invention as defined in the claims that follow.

What is claimed is:

1. A pyridyl imidazole compound, and pharmacologically acceptable salts thereof, of formula(I):

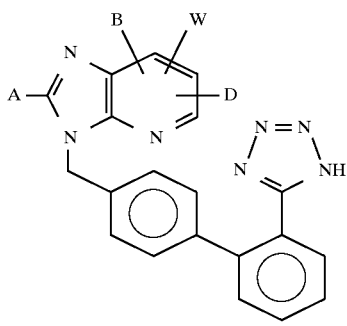

wherein: A is a straight, branched or cyclic $C_1$–$C_6$ alkyl group, or $OR_1$, or $NR_2R_3$ wherein $R_1$, $R_2$ and $R_3$ are independently a hydrogen, or a straight, branched or cyclic $C_1$–$C_6$ alkyl group; B is a hydrogen, or a straight, branched or cyclic $C_1$–$C_6$ alkyl group; D is a hydrogen, a halogen, or a straight, branched or cyclic $C_1$–$C_6$ alkyl group, or

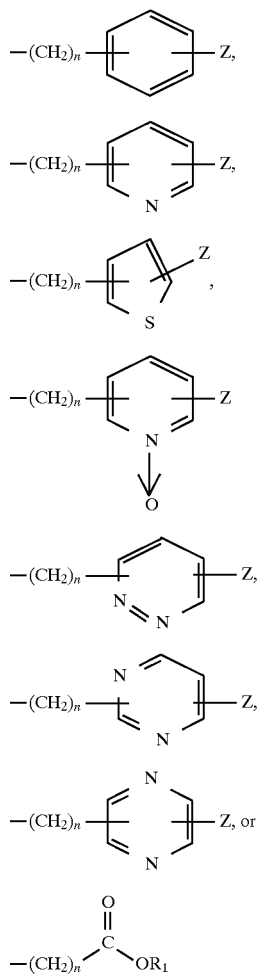

wherein Z is a hydrogen, or $R_1$, $NO_2$, $(CH_2)_pOR_5$, $(CH_2)_pNR_2R_3$ or a halogen, n is 0 or an integer of 1 to 3, $R_1$, $R_2$ and $R_3$ are the same as defined above, p is 0 or an integer of 1 to 3, and $R_5$ is a hydrogen, a $C_1$–$C_6$ alkyl group or a phenyl group substituted with a $C_1$–$C_4$ alkyl; and W is

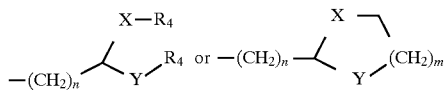

wherein X and Y are independently O or S, m is an integer of 1 to 4, n is the same as defined above and $R_4$ is a straight, branched or cyclic $C_1$–$C_4$ alkyl group.

2. The compound of claim 1 wherein A is a straight, branched or cyclic $C_2$–$C_4$ alkyl group or $OR_1$ wherein $R_1$ is a straight, branched or cyclic $C_1$–$C_4$ alkyl group; B is a hydrogen or a straight, branched or cyclic $C_1$–$C_4$ alkyl group; and D is H, F, Br, Cl, or a straight, branched or cyclic $C_1$–$C_6$ alkyl group, or

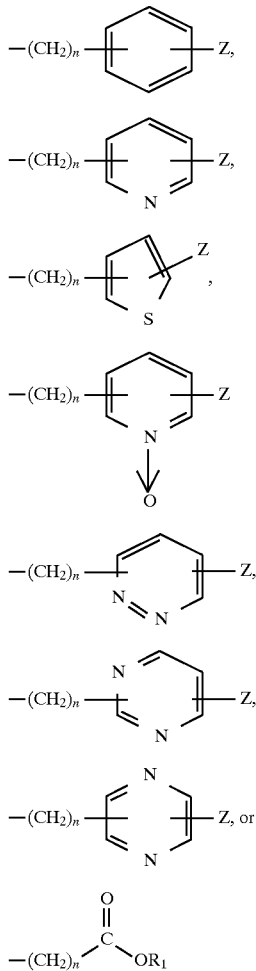

wherein Z is a hydrogen, $R_1$, $NO_2$, $(CH_2)_pOR_5$, F, Br or Cl, n is 0, 1 or 2, $R_1$ is the same as defined in claim 1, p is 0, 1 or 2, and $R_5$ is a hydrogen, a $C_1$–$C_4$ alkyl group or a phenyl group substituted with a $C_1$–$C_4$ alkyl; and W is

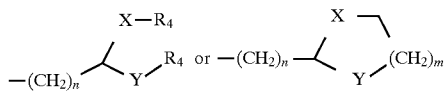

wherein X and Y are independently O or S, m is an integer of 1 to 3, n is the same as defined in claim 1 and $R_4$ is a straight, branched or cyclic $C_1$–$C_4$ alkyl group.

3. The compound of claim 1 which is selected from the group consisting of:

2-butyl-5-dimethoxymethyl-6-phenyl-3-[2'-(1H-tetrazol-5-yl)-biphenyl-4-ylmethyl]-3H-imidazo[4,5-b]pyridine;
2-butyl-5-diethoxymethyl-6-phenyl-3-[2'-(1H-tetrazol-5-yl)-biphenyl-4-ylmethyl]-3H-imidazo[4,5-b]pyridine;
2-butyl-5-(1,3-dioxolan-2-yl)-6-phenyl-3-[2'-(1H-tetrazol-5-yl)-biphenyl-4-ylmethyl]-3H-imidazo[4,5-b]pyridine;
2-butyl-5-(1,3-dioxan-2-yl)-6-phenyl-3-[2'-(1H-tetrazol-5-yl)-biphenyl-4-ylmethyl]-3H-imidazo[4,5-b]pyridine;
2-butyl-5-dimethoxymethyl-6-(4-hydroxymethylphenyl-1-yl)-3-[2'-(1H-tetrazol-5-yl)-biphenyl-4-ylmethyl]-3H-imidazo[4,5-b]pyridine;
2-butyl-5-dimethoxymethyl-6-(4-benzyloxymethylphenyl-1-yl)-3-[2'-(1H-tetrazol-5-yl)-biphenyl-4-ylmethyl]-3H-imidazo[4,5-b]pyridine;
2-butyl-5-dimethoxymethyl-6-(2-methoxyphenyl-1-yl)-3-[2'-(1H-tetrazol-5-yl)-biphenyl-4-ylmethyl]-3H-imidazo[4,5-b]pyridine;
2-butyl-5-dimethoxymethyl-6-(4-methoxyphenyl-1-yl)-3-[2'-(1H-tetrazol-5-yl)-biphenyl-4-ylmethyl]-3H-imidazo[4,5-b]pyridine;
2-butyl-5-dimethoxymethyl-6-(2-nitrophenyl-1-yl)-3-[2'-(1H-tetrazol-5-yl)-biphenyl-4-ylmethyl]-3H-imidazo[4,5-b]pyridine;
2-butyl-5-dimethoxymethyl-6-(2-aminophenyl-1-yl)-3-[2'-(1H-tetrazol-5-yl)-biphenyl-4-ylmethyl]-3H-imidazo[4,5-b]pyridine;
2-butyl-5-dimethoxymethyl-6-(2-phenylethyl-1-yl)-3-[2'-(1H-tetrazol-5-yl)-biphenyl-4-ylmethyl]-3H-imidazo[4,5-b]pyridine;
2-butyl-5-dimethoxymethyl-6-benzyl-3-[2'-(1H-tetrazol-5-yl)-biphenyl-4-ylmethyl]-3H-imidazo[4,5-b]pyridine;
2-butyl-5-dimethoxymethyl-6-(pyridin-2-yl)-3-[2'-(1H-tetrazol-5-yl)-biphenyl-4-ylmethyl]-3H-imidazo[4,5-b]pyridine;
2-butyl-5-dimethoxymethyl-6-(pyridin-3-yl)-3-[2'-(1H-tetrazol-5-yl)-biphenyl-4-ylmethyl]-3H-imidazo[4,5-b]pyridine;
2-butyl-5-dimethoxymethyl-6-(pyridin-4-yl)-3-[2'-(1H-tetrazol-5-yl)-biphenyl-4-ylmethyl]-3H-imidazo[4,5-b]pyridine;
2-butyl-5-dimethoxymethyl-6-(1-oxopyridin-2-yl)-3-[2'-(1H-tetrazol-5-yl)-biphenyl-4-ylmethyl]-3H-imidazo[4,5-b]pyridine;
2-butyl-5-dimethoxymethyl-6-(1-oxopyridin-3-yl)-3-[2'-(1H-tetrazol-5-yl)-biphenyl-4-ylmethyl]-3H-imidazo[4,5-b]pyridine;
2-butyl-5-dimethoxymethyl-6-(1-oxopyridin-4-yl)-3-[2'-(1H-tetrazol-5-yl)-biphenyl-4-ylmethyl]-3H-imidazo[4,5-b]pyridine;
2-butyl-5-diethoxymethyl-6-(pyridin-2-yl)-3-[2'-(1H-tetrazol-5-yl)-biphenyl-4-ylmethyl]-3H-imidazo[4,5-b]pyridine;
2-butyl-5-(1,3-dioxolan-2-yl)-6-(pyridin-2-yl)-3-[2'-(1H-tetrazol-5-yl)-biphenyl-4-ylmethyl]-3H-imidazo[4,5-b]pyridine;
2-butyl-5-(1,3-dioxan-2-yl)-6-(pyridin-2-yl)-3-[2'-(1H-tetrazol-5-yl)-biphenyl-4-ylmethyl]-3H-imidazo[4,5-b]pyridine;
2-butyl-5-diethoxymethyl-6-(pyridin-3-yl)-3-[2'-(1H-tetrazol-5-yl)-biphenyl-4-ylmethyl]-3H-imidazo[4,5-b]pyridine;
2-butyl-5-(1,3-dioxolan-2-yl)-6-(pyridin-3-yl)-3-[2'-(1H-tetrazol-5-yl)-biphenyl-4-ylmethyl]-3H-imidazo[4,5-b]pyridine;
2-butyl-5-(1,3-dioxan-2-yl)-6-(pyridin-3-yl)-3-[2'-(1H-tetrazol-5-yl)-biphenyl-4-ylmethyl]-3H-imidazo[4,5-b]pyridine;
2-butyl-5-diethoxymethyl-6-(pyridin-4-yl)-3-[2'-(1H-tetrazol-5-yl)-biphenyl-4-ylmethyl]-3H-imidazo[4,5-b]pyridine;

2-butyl-5-(1,3-dioxolan-2-yl)-6-(pyridin-4-yl)-3-[2'-(1H-tetrazol-5-yl)-biphenyl-4-ylmethyl]-3H-imidazo[4,5-b]pyridine;
2-butyl-5-(1,3-dioxan-2-yl)-6-(pyridin-4-yl)-3-[2'-(1H-tetrazol-5-yl)-biphenyl-4-ylmethyl]-3H-imidazo[4,5-b]pyridine;
2-ethoxy-5-dimethoxymethyl-6-phenyl-3-[2'-(1H-tetrazol-5-yl)-biphenyl-4-ylmethyl]-3H-imidazo[4,5-b]pyridine;
2-ethoxy-5-dimethoxymethyl-6-(pyridin-2-yl)-3-[2'-(1H-tetrazol-5-yl)-biphenyl-4-ylmethyl]-3H-imidazo[4,5-b]pyridine;
2-ethoxy-5-dimethoxymethyl-6-(1-oxopyridin-4-yl)-3-[2'-(1H-tetrazol-5-yl)-biphenyl-4-ylmethyl]-3H-imidazo[4,5-b]pyridine;
2-butyl-5-dimethoxymethyl-3-[2'-(1H-tetrazol-5-yl)-biphenyl-4-ylmethyl]-3H-imidazo[4,5-b]pyridine;
2-butyl-5-dimethoxymethyl-6-bromo-3-[2'-(1H-tetrazol-5-yl)-biphenyl-4-ylmethyl]-3H-imidazo[4,5-b]pyridine;
2-butyl-5-dimethoxymethyl-6-phenyl-7-methyl-3-[2'-(1H-tetrazol-5-yl)-biphenyl-4-ylmethyl]-3H-imidazo[4,5-b]pyridine;
2-butyl-5-dimethoxymethyl-6-(pyridin-2-yl)-7-methyl-3-[2'-(1H-tetrazol-5-yl)-biphenyl-4-ylmethyl]-3H-imidazo[4,5-b]pyridine;
2-butyl-5-methyl-6-phenyl-7-dimethoxymethyl-3-[2'-(1H-tetrazol-5-yl)-biphenyl-4-ylmethyl]-3H-imidazo[4,5-b]pyridine;
2-butyl-5-dimethoxymethyl-6-[2-(ethoxycarbonyl)-ethyl-1-yl]-3-[2'-(1H-tetrazol-5-yl)-biphenyl-4-ylmethyl]-3H-imidazo[4,5-b]pyridine; and mixtures thereof.

4. The compound of claim 3 which is selected from the group consisting of:
2-butyl-5-dimethoxymethyl-6-phenyl-3-[2'-(1H-tetrazol-5-yl)-biphenyl-4-ylmethyl]-3H-imidazo[4,5-b]pyridine;
2-butyl-5-dimethoxymethyl-6-(4-hydroxymethylphenyl-1-yl)-3-[2'-(1H-tetrazol-5-yl)-biphenyl-4-ylmethyl ]-3H-imidazo [4,5-b]pyridine;
2-butyl-5-dimethoxymethyl-6-(4-benzyloxymethylphenyl-1-yl)-3-[2'-(1H-tetrazol-5-yl)-biphenyl-4-ylmethyl]-3H-imidazo [4,5-b]pyridine;
2-butyl-5-dimethoxymethyl-6-(2-methoxyphenyl-1-yl)-3-[2'-(1H-tetrazol-5-yl)-biphenyl-4-ylmethyl]-3H-imidazo[4,5-b]pyridine;
2-butyl-5-dimethoxymethyl-6-(4-methoxyphenyl-1-yl)-3-[2'-(1H-tetrazol-5-yl)-biphenyl-4-ylmethyl]-3H-imidazo[4,5-b]pyridine;
2-butyl-5-dimethoxymethyl-6-(2-nitrophenyl-1-yl)-3-[2'-(1H-tetrazol-5-yl)-biphenyl-4-ylmethyl]-3H-imidazo[4,5-b]pyridine;
2-butyl-5-dimethoxymethyl-6-(2-aminophenyl-1-yl)-3-[2'-(1H-tetrazol-5-yl)-biphenyl-4-ylmethyl]-3H-imidazo[4,5-b]pyridine;
2-butyl-5-dimethoxymethyl-6-(2-phenylethyl-1-yl)-3-[2'-(1H-tetrazol-5-yl)-biphenyl-4-ylmethyl]-3H-imidazo[4,5-b]pyridine;
2-butyl-5-dimethoxymethyl-6-(pyridin-2-yl)-3-[2'-(1H-tetrazol-5-yl)-biphenyl-4-ylmethyl]-3H-imidazo[4,5-b]pyridine;
2-butyl-5-dimethoxymethyl-6-(pyridin-3-yl)-3-[2'-(1H-tetrazol-5-yl)-biphenyl-4-ylmethyl]-3H-imidazo[4,5-b]pyridine;
2-butyl-5-dimethoxymethyl-6-(pyridin-4-yl)-3-[2'-(1H-tetrazol-5-yl)-biphenyl-4-ylmethyl]-3H-imidazo[4,5-b]pyridine;
2-butyl-5-dimethoxymethyl-6-(1-oxopyridin-2-yl)-3-[2'-(1H-tetrazol-5-yl)-biphenyl-4-ylmethyl]-3H-imidazo[4,5-b]pyridine;
2-butyl-5-dimethoxymethyl-6-(1-oxopyridin-3-yl)-3-[2'-(1H-tetrazol-5-yl)-biphenyl-4-ylmethyl]-3H-imidazo[4,5-b]pyridine;
2-butyl-5-dimethoxymethyl-6-(1-oxopyridin-4-yl)-3-[2'-(1H-tetrazol-5-yl)-biphenyl-4-ylmethyl]-3H-imidazo[4,5-b]pyridine;
2-butyl-5-dimethoxymethyl-6-phenyl-7-methyl-3-[2'-(1H-tetrazol-5-yl)-biphenyl-4-ylmethyl]-3H-imidazo[4,5-b]pyridine;
2-butyl-5-dimethoxymethyl-6-(pyridin-2-yl)-7-methyl-3-[2'-(1H-tetrazol-5-yl)-biphenyl-4-ylmethyl]-3H-imidazo[4,5-b]pyridine;
2-butyl-5-methyl-6-phenyl-7-dimethoxymethyl-3-[2'-(1H-tetrazol-5-yl)-biphenyl-4-ylmethyl]-3H-imidazo[4,5-b]pyridine;
2-butyl-5-dimethoxymethyl-6-[2-(ethoxycarbonyl)-ethyl-1-yl]-3-[2'-(1H-tetrazol-5-yl)-biphenyl-4-ylmethyl]-3H-imidazo[4,5-b]pyridine; and mixtures thereof.

5. The compound of claim 4 which is selected from the group consisting of:
2-butyl-5-dimethoxymethyl-6-phenyl-3-[2'-(1H-tetrazol-5-yl)-biphenyl-4-ylmethyl]-3H-imidazo[4,5-b]pyridine;
2-butyl-5-dimethoxymethyl-6-(2-phenylethyl-1-yl)-3-[2'-(1H-tetrazol-5-yl)-biphenyl-4-ylmethyl]-3H-imidazo[4,5-b]pyridine;
2-butyl-5-dimethoxymethyl-6-(pyridin-2-yl)-3-[2'-(1H-tetrazol-5-yl)-biphenyl-4-ylmethyl]-3H-imidazo[4,5-b]pyridine;
2-butyl-5-dimethoxymethyl-6-(pyridin-3-yl)-3-[2'-(1H-tetrazol-5-yl)-biphenyl-4-ylmethyl]-3H-imidazo[4,5-b]pyridine;
2-butyl-5-dimethoxymethyl-6-(pyridin-4-yl)-3-[2'-(1H-tetrazol-5-yl)-biphenyl-4-ylmethyl]-3H-imidazo[4,5-b]pyridine;
2-butyl-5-dimethoxymethyl-6-(1-oxopyridin-4-yl)-3-[2'-(1H-tetrazol-5-yl)-biphenyl-4-ylmethyl]-3H-imidazo[4,5-b]pyridine;
2-butyl-5-dimethoxymethyl-6-phenyl-7-methyl-3-[2'-(1H-tetrazol-5-yl)--biphenyl-4-ylmethyl]-3H-imidazo[4,5-b]pyridine;
2-butyl-5-methyl-6-phenyl-7-dimethoxymethyl-3-[2'-(1H-tetrazol-5-yl)-biphenyl-4-ylmethyl]-3H-imidazo[4,5-b]pyridine; and mixtures thereof.

6. A process for preparing a compound of formula(I-1) which comprises reacting a compound of formula(XIV) with $R_4XH$ or $HXCH_2(CH_2)_mYH$:

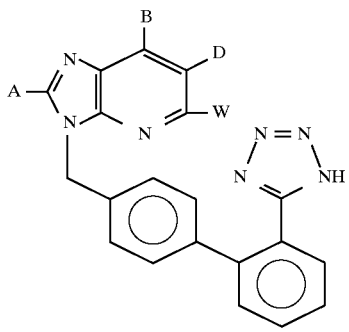

-continued

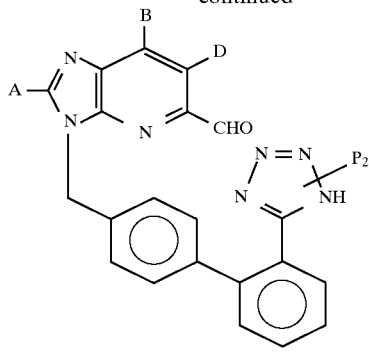
(XIV)

wherein: A, B, D, W, $R_4$, X, Y and m are the same as defined in claim 1; n is 0; and $P_2$ is a protecting group.

7. A process for preparing a compound of formula(I-1) which comprises reacting a compound of formula(XX) with $R_4XH$ or $HXCH_2(CH_2)_mYH$:

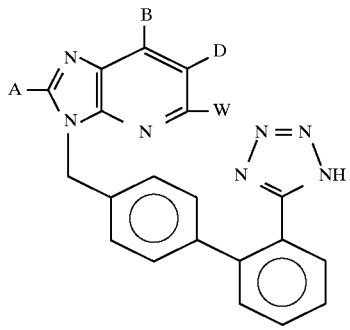
(I-1)

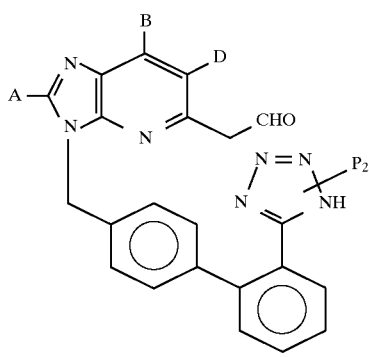
(XX)

wherein: A, B, D, W, $R_4$, X, Y and m are the same as defined in claim 1; and n is 1.

8. A process for preparing a compound of formula(I-1) which comprises reacting a compound of formula(XXIII) with $R_4XH$ or $HXCH_2(CH_2)_mYH$:

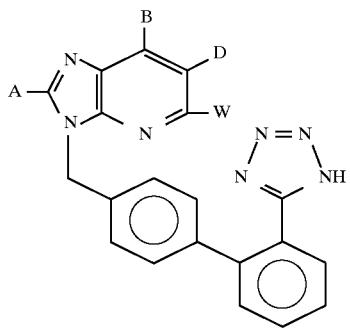
(I-1)

-continued

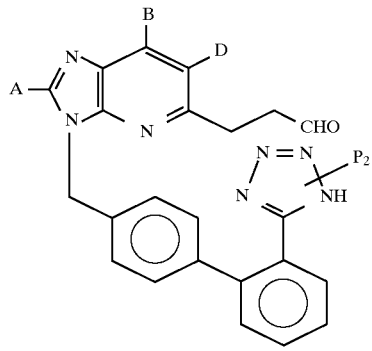
(XXIII)

wherein: A, B, D, W, $R_4$, X, Y and m are the same as defined in claim 1; and n is 2.

9. A process for preparing a compound of formula(I-1) which comprises reacting a compound of formula(XXV) with $R_4XH$ or $HXCH_2(CH_2)_mYH$:

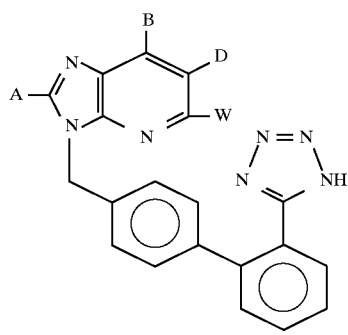
(I-1)

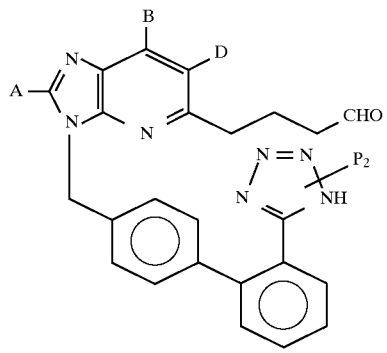
(XXV)

wherein: A, B, D, W, $R_4$, X, Y and m are the same as defined in claim 1; and n is 3.

10. A composition comprising a therapeutically effective amount of the pyridyl imidazole compound of claim 1 and a pharmaceutically acceptable carrier or adjuvant.

* * * * *